United States Patent
Borrebaeck et al.

(10) Patent No.: US 9,388,469 B2
(45) Date of Patent: Jul. 12, 2016

(54) SOX11 EXPRESSION IN MALIGNANT LYMPHOMAS

(75) Inventors: Carl Arne Krister Borrebaeck, Lund (SE); Sara Ek, Lund (SE)

(73) Assignee: Immunovia AB, Lund (SE)

( * ) Notice: Subject to any disclaimer, the term of this patent is extended or adjusted under 35 U.S.C. 154(b) by 352 days.

(21) Appl. No.: 12/598,221

(22) PCT Filed: May 12, 2008

(86) PCT No.: PCT/GB2008/001625
§ 371 (c)(1),
(2), (4) Date: Oct. 30, 2009

(87) PCT Pub. No.: WO2008/139169
PCT Pub. Date: Nov. 20, 2008

(65) Prior Publication Data
US 2010/0119449 A1    May 13, 2010

(30) Foreign Application Priority Data
May 11, 2007  (GB) .................................. 0709092.1

(51) Int. Cl.
*C12Q 1/68* (2006.01)
*G01N 33/574* (2006.01)
*C07K 16/00* (2006.01)
*A61K 51/10* (2006.01)

(52) U.S. Cl.
CPC .......... *C12Q 1/6886* (2013.01); *A61K 51/1069* (2013.01); *C07K 16/00* (2013.01); *G01N 33/57496* (2013.01); *C12Q 2600/118* (2013.01); *C12Q 2600/158* (2013.01); *G01N 2500/20* (2013.01); *G01N 2800/52* (2013.01)

(58) Field of Classification Search
CPC ....... C12Q 1/68; G01N 33/53; G01N 33/574; A61K 49/00
USPC ................... 424/9.1; 435/6, 4, 7.1, 7.23, 6.14
See application file for complete search history.

(56) References Cited

U.S. PATENT DOCUMENTS

| | | | |
|---|---|---|---|
| 4,376,110 A | 3/1983 | David et al. | |
| 4,486,530 A | 12/1984 | David et al. | |
| 2003/0105000 A1* | 6/2003 | Pero et al. | ........................ 514/12 |
| 2005/0164231 A1 | 7/2005 | Staudt et al. | |
| 2006/0019256 A1* | 1/2006 | Clarke et al. | ........................ 435/6 |

FOREIGN PATENT DOCUMENTS

| | | |
|---|---|---|
| WO | 2004/060304 | 7/2004 |
| WO | 2005/002417 | 1/2005 |

OTHER PUBLICATIONS

Tan (Pathology, Jun. 2009, 41(4), pp. 305-326).*
Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Rudikoff et al, (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Burgess et al (J of Cell Bio. 111:2129-2138, 1990).*
Chen et al. (J Nucl Med. Jun. 1990;31(6):1059-66).*
Agaton, C., et al. "Affinity proteomics for systematic protein profiling of chromosome 21 gene products in human tissues." Mol Cell Proteomics. Jun. 2003;2(6):405-14. Epub Jun. 9, 2003.
Alizadeh, A.A., et al. "Distinct types of diffuse large B-cell lymphoma identified by gene expression profiling." Nature. Feb. 3, 2000;403(6769):503-11.
Ambrosetti, D.C., et al. "Synergistic activation of the fibroblast growth factor 4 enhancer by Sox2 and Oct-3 depends on protein-protein interactions facilitated by a specific spatial arrangement of factor binding sites." Mol Cell Biol. Nov. 1997;17(11):6321-9.
Andreasson, U., et al. "B cell lymphomas express CX3CR1 a non-B cell lineage adhesion molecule." Cancer Lett. Feb. 8, 2008;259(2):138-45. Epub Dec. 3, 2007.
Azuma, T., et al. "Human SOX11, an upregulated gene during the neural differentiation, has a long 3' untranslated region." DNA Res. Oct. 29, 1999;6(5):357-60.
Becker, D.M., et al. "High-efficiency transformation of yeast by electroporation." Methods Enzymol. 1991;194:182-7.
Better, M., et al. "*Escherichia coli* secretion of an active chimeric antibody fragment." Science. May 20, 1988;240 (4855):1041-3.
Bird, R.E., et al. "Single-chain antigen-binding proteins." Science. Oct. 21, 1988;242(4877):423-6.
Capello, D., et al. "Molecular pathophysiology of indolent lymphoma." Haematologica. Feb. 2000;85(2):195-201.
Chang, C.H., et al. "ESX: a structurally unique Ets overexpressed early during human breast tumorigenesis." Oncogene. Apr. 3, 1997;14(13):1617-22.

(Continued)

*Primary Examiner* — Yan Xiao
(74) *Attorney, Agent, or Firm* — Patrick J. Hagan; Dann, Dorfman, Herrell and Skillman, P.C.

(57) ABSTRACT

The present invention provides a binding moiety which selectively binds to Sox11 protein and/or mRNA for imaging, diagnosis or prognosis of lymphomas, such as mantle cell lymphomas (MCL) and diffuse large B-cell lymphoma (DL-BCL). Optionally, the moiety is an antibody or antigen-binding fragment thereof. Advantageously, moiety comprises a further, readily detectable moiety. The invention also provides methods of imaging lymphomas cells as well as methods of diagnosing or prognosing lymphomas in an individual. A further aspect of the present invention provides a method of identifying cells associated with lymphomas, the method comprising analyzing the pattern of gene expression in a sample of cells to be tested and comparing it to the pattern of gene expression in a sample of known lymphomas cells. Preferably, the cells to be tested are identified as lymphoma cells if the expression of Sox11 is upregulated compared to normal B-cells.

10 Claims, 12 Drawing Sheets

(56) References Cited

OTHER PUBLICATIONS

Figure 1:
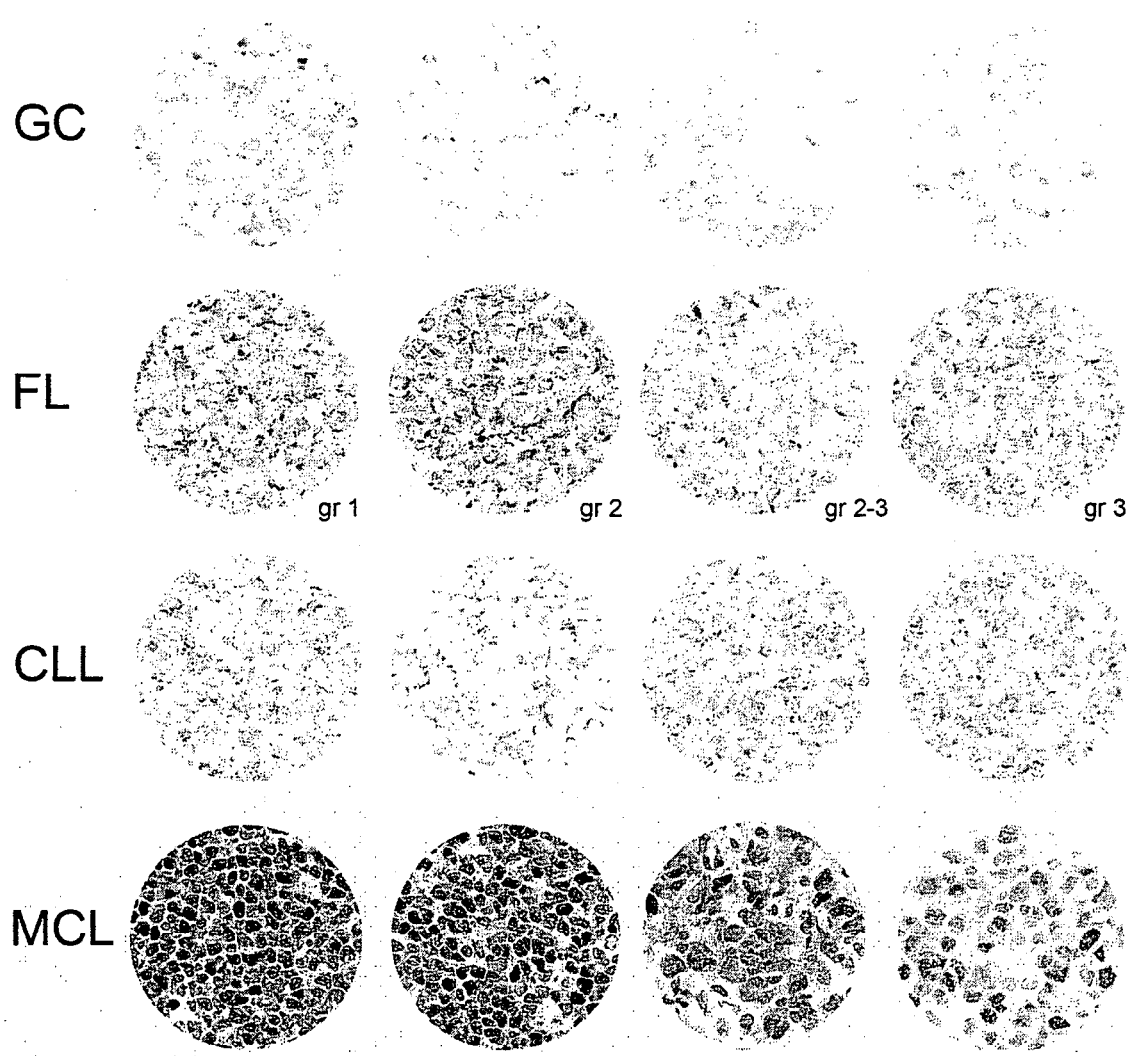

Chatal, J.F., et al. "Biodistribution of indium-111-labeled OC 125 monoclonal antibody intraperitoneally injected into patients operated on for ovarian carcinomas." Cancer Res. Jun. 1, 1989;49(11):3087-94.

Cheuk, W., et al. "Consistent immunostaining for cyclin D1 can be achieved on a routine basis using a newly available rabbit monoclonal antibody." Am J Surg Pathol. Jun. 2004;28(6):801-7.

Cheung, M., et al. "Roles of Sox4 in central nervous system development." Brain Res Mol Brain Res. Jun. 23, 2000;79 (1-2):180-91.

De Boer, C.J., et al. "Involvement of the CCND1 gene in hairy cell leukemia." Ann Oncol. Mar. 1996;7(3):251-6.

Dong, C., et al. "Sox genes and cancer." Cytogenet Genome Res. 2004;105(2-4):442-7.

Donnellan, R., et al. "Cyclin D1 and human neoplasia." Mol Pathol. Feb. 1998;51(1):1-7.

Ek, S., et al. "Parallel gene expression profiling of mantle cell lymphoma—how do we transform 'omics data into clinical practice." Curr Genomics. May 2007;8(3):171-9.

Ek, S., et al. "Mantle cell lymphomas express a distinct genetic signature affecting lymphocyte trafficking and growth regulation as compared with subpopulations of normal human B cells." Cancer Res. Aug. 1, 2002;62(15):4398-405.

Ek, S., et al. "From gene expression analysis to tissue microarrays: a rational approach to identify therapeutic and diagnostic targets in lymphoid malignancies." Mol Cell Proteomics. Jun. 2006;5(6):1072-81. Epub Mar. 8, 2006.

Ek, S., et al. "Nuclear expression of the non B-cell lineage Sox11 transcription factor identifies mantle cell lymphoma." Blood. Jan. 15, 2008;111(2):800-5. Epub Oct. 12, 2007.

Fraker, P.J., et al. "Protein and cell membrane iodinations with a sparingly soluble chloroamide, 1,3,4,6-tetrachloro-3a,6a-diphrenylglycoluril." Biochem Biophys Res Commun. Feb. 28, 1978;80(4):849-57.

Fu, K., et al. "Cyclin D1-negative mantle cell lymphoma: a clinicopathologic study based on gene expression profiling." Blood. Dec. 15, 2005;106(13):4315-21. Epub Aug. 25, 2005.

Gasca, S., et al. "A nuclear export signal within the high mobility group domain regulates the nucleocytoplasmic translocation of SOX9 during sexual determination." Proc Natl Acad Sci U S A. Aug. 20, 2002;99(17):11199-204. Epub Aug. 8, 2002.

Gietz, R.D., et al. "Genetic transformation of yeast." Biotechniques. Apr. 2001;30(4):816-20, 822-6, 828 passim.

Golub, T.R., et al. "Molecular classification of cancer: class discovery and class prediction by gene expression monitoring." Science. Oct. 15, 1999;286(5439):531-7.

Harley, V.R., et al. "Definition of a consensus DNA binding site for SRY." Nucleic Acids Res. Apr. 25, 1994;22 (8):1500-1.

Harris, N. L., et al. "A revised European-American classification of lymphoid neoplasms: a proposal from the International Lymphoma Study Group." Blood. Sep. 1, 1994;84(5):1361-92.

Harris, N. L., et al. "The World Health Organization classification of hematological malignancies report of the Clinical Advisory Committee Meeting, Airlie House, Virginia, Nov. 1997." Mod Pathol. Feb. 2000;13(2):193-207.

Heckman, C.A., et al. "Oct transcription factors mediate t(14;18) lymphoma cell survival by directly regulating bcl-2 expression." Oncogene. Feb. 9, 2006;25(6):888-98.

Huang, S.L., et al. "Study of intrauterine cytomegaloviruses infection in pregnant women and fetuses." Zhonghua Fu Chan Ke Za Zhi. Nov. 1990;25(6):337-9, 382-3.

Hubbard, T., et al. "Ensembl 2005." Nucleic Acids Res. Jan. 1, 2005;33(Database issue):D447-53.

Huston, J.S., et al. "Protein engineering of antibody binding sites: recovery of specific activity in an anti-digoxin single-chain Fv analogue produced in *Escherichia coli*." Proc Natl Acad Sci U S A. Aug. 1988;85(16):5879-83.

Iguchi, H., et al. "SOX6 suppresses cyclin D1 promoter activity by interacting with beta-catenin and histone deacetylase 1, and its downregulation induces pancreatic beta-cell proliferation." J Biol Chem. Jun. 29, 2007;282 (26):19052-61. Epub Apr. 4, 2007.

Jankowski, M.P., et al. "SRY-box containing gene 11 (Sox11) transcription factor is required for neuron survival and neurite growth." Neuroscience. Dec. 1, 2006;143(2):501-14. Epub Oct. 19, 2006.

Jay, P., et al. "The human SOX11 gene: cloning, chromosomal assignment and tissue expression." Genomics. Sep. 20, 1995;29(2):541-5.

Kuhlbrodt, K., et al. "Cooperative function of POU proteins and SOX proteins in glial cells." J Biol Chem. Jun. 26, 1998;273(26):16050-7.

Kurtin, P.J. "Mantle cell lymphoma." Adv Anat Pathol. Nov. 1998;5(6):376-98.

Larue, L., et al. "The WNT/Beta-catenin pathway in melanoma." Front Biosci. Jan. 1, 2006;11:733-42.

Lee, C.J., et al. "Differential expression of SOX4 and SOX11 in medulloblastoma." J Neurooncol. May 2002;57 (3):201-14.

Lindskog, M., et al. "Selection of protein epitopes for antibody production." Biotechniques. May 2005;38(5):723-7.

Livak, K.J., et al. "Analysis of relative gene expression data using real-time quantitative PCR and the 2(-Delta Delta C (T)) Method." Methods. Dec. 2001;25(4):402-8.

Luchansky, J.B., et al. "Application of electroporation for transfer of plasmid DNA to Lactobacillus, Lactococcus, Leuconostoc, Listeria, Pediococcus, Bacillus, *Staphylococcus*, Enterococcus and Propionibacterium." Mol Microbiol. Sep. 1998;2(5):637-46.

Morrison, S.L., et al. "Chimeric human antibody molecules: mouse antigen-binding domains with human constant region domains." Proc Natl Acad Sci U S A. Nov. 1984;81(21):6851-5.

NCBI accession No. U23752, Sep. 20, 1996.

Neuberger, M.S., et al. 8th International Biotechnology Symposium, Part 2, 1998; 792-799.

Nilsson, P., et al. "Towards a human proteome atlas: high-throughput generation of mono-specific antibodies for tissue profiling." Proteomics. Nov. 2005;5(17):4327-37.

Pascual, V., et al. "Normal human B cell sub-populations and their malignant counterparts." Baillieres Clin Haematol. Sep. 1997;10(3):525-38.

Poulat, F., et al. "Nuclear localization of the testis determining gene product SRY." J Cell Biol. Mar. 1995;128 (5):737-48.

Rehberg, S., et al. "Sox10 is an active nucleocytoplasmic shuttle protein, and shuttling is crucial for Sox10-mediated transactivation." Mol Cell Biol. Aug. 2002;22(16):5826-34.

Skerra, A., et al. "Assembly of a functional immunoglobulin Fv fragment in *Escherichia coli*." Science. May 20, 1988;240(4855):1038-41.

Smith, E., et al. "The roles of transcription factors in B lymphocyte commitment, development, and transformation." J Leukoc Biol. Jun. 2004;75(6):973-81. Epub Feb. 24, 2004.

Sock, E., et al. "Gene targeting reveals a widespread role for the high-mobility-group transcription factor Sox11 in tissue remodeling." Mol Cell Biol. Aug. 2004;24(15):6635-44.

Stacey, D.W. "Cyclin D1 serves as a cell cycle regulatory switch in actively proliferating cells." Curr Opin Cell Biol. Apr. 2003;15(2):158-63.

Südbeck, P., et al. "Two independent nuclear localization signals are present in the DNA-binding high-mobility group domains of SRY and SOX9." J Biol Chem. Oct. 31, 1997;272(44):27848-52.

Uhlén, M., et al. "A human protein atlas for normal and cancer tissues based on antibody proteomics." Mol Cell Proteomics. Dec. 2005;4(12):1920-32. Epub Aug. 27, 2005.

Van De Wetering, M., et al. "Sox-4, an Sry-like HMG box protein, is a transcriptional activator in lymphocytes." EMBO J. Oct. 1993;12(10):3847-54.

Van Dongen, J.J., et al. "Design and standardization of PCR primers and protocols for detection of clonal immunoglobulin and T-cell receptor gene recombinations in suspect lymphoproliferations: report of the BIOMED-2 Concerted Action BMH4-CT98-3936." Leukemia. Dec. 2003;17(12):2257-317.

Vaughan, T.J., et al. "Human antibodies by design." Nat Biotechnol. Jun. 1998;16(6):535-9.

Ventura, R.A., et al. "FISH analysis for the detection of lymphoma-associated chromosomal abnormalities in routine paraffin-embedded tissue." J Mol Diagn. May 2006;8(2):141-51.

(56) References Cited

OTHER PUBLICATIONS

Ward, E.S., et al. "Binding activities of a repertoire of single immunoglobulin variable domains secreted from *Escherichia coli*." Nature. Oct. 12, 1989;341(6242):544-6.

Wegner, M. "From head to toes: the multiple facets of Sox proteins." Nucleic Acids Res. Mar. 15, 1999;27(6):1409-20.

Wegner, M. "Secrets to a healthy Sox life: lessons for melanocytes." Pigment Cell Res. Apr. 2005;18(2):74-85.

Weigle, B., et al. "Highly specific overexpression of the transcription factor SOX11 in human malignant gliomas." Oncol Rep. Jan. 2005;13(1):139-44.

Weisenburger, D.D., et al. "Mantle cell lymphoma. A clinicopathologic study of 68 cases from the Nebraska Lymphoma Study Group." Am J Hematol. Jul. 2000;64(3):190-6.

Werner, M.H., et al. "Molecular basis of human 46X,Y sex reversal revealed from the three-dimensional solution structure of the human SRY-DNA complex." Cell. Jun. 2, 1995;81(5):705-14.

Wiebe, M.S., et al. "Identification of novel domains within Sox-2 and Sox-11 involved in autoinhibition of DNA binding and partnership specificity." J Biol Chem. May 16, 2003;278(20):17901-11. Epub Mar. 10, 2003.

Winter, G., et al. "Man-made antibodies." Nature. Jan. 24, 1991;349(6307):293-9.

Xia, Y., et al. "The oncogenic potential of the high mobility group box protein Sox3." Cancer Res. Nov. 15, 2000;60 (22):6303-6.

Yatabe, Y., et al. "Significance of cyclin D1 overexpression for the diagnosis of mantle cell lymphoma: a clinicopathologic comparison of cyclin D1-positive MCL and cyclin D1-negative MCL-like B-cell lymphoma." Blood. Apr. 1, 2000;95(7):2253-61.

"LALIGN—find multiple matching subsegments in two sequences." http://www.ch.embnet.org/software/LALIGN_form.html.

* cited by examiner

MVQQAESLEAESNLPREALDTEEGEFMACSPVALDESDPDWCKTASGHIKR
PMNAFMVWSKIERRKIMEQSPDMHNAEISKRLGKRWKMLKDSEKIPFIREAE
RLRLKHMADYPDYKYRPRKKPKMDPSAKPSASQSPEKSAAGGGGGSAGG
GAGGAKTSKGSSKKCGKLKAPAAAGAKAGAGKAAQSGDYGGAGDDYVLG
SLRVSGSGGGGAGKTVKCVFLDEDDDDDDDDELQLQIKQEPDEEDEEPP
HQQLLQPPGQQPSQLLRRYNVAKVPASPTLSSSAESPEGASLYDEVRAGAT
SGAGGGSRLYYSFKNITKQHPPPLAQPALSPASSRSVSTSSSSSSGSSSGS
SGEDADDLMFDLSLNFSQSAHSASEQQLGGGAAAGNLSLSLVDKDLDSFSE
GSLGSHFEFPDYCTPELSEMIAGDWLEANFSDLVFTY

SEQ ID NO:1

*Figure 4*

```
acctccgcacgagacccagcggcccggggttggagcgtccagccctgcagcggatcat
ggtgcagcaggcggagagcttggaagcggagagcaacctgccccgggaggcgctgga
cacggaggagggcgaattcatggcttgcagcccggtggccctggacgagagcgaccc
agactggtgcaagacggcgtcgggccacatcaagcggccgatgaacgcgttcatggt
atggtccaagatcgaacgcaggaagatcatggagcagtctccggacatgcacaacgc
cgagatctccaagaggctgggcaagcgctggaaaatgctgaaggacagcgagaagat
cccgttcatccggggaggcggagcggctgcggctcaagcacatggccgactacccga
ctacaagtaccggccccggaaaaagcccaaatggacccctcggccaagcccagcgc
cagccagagcccagagaagagcgcggccggcggcggcggcgggagcgcgggcggagg
cgcgggcggtgccaagacctccaagggctccagcaagaaatgcggcaagctcaaggc
ccccgcggccgcgggcgccaaggcgggcgcgggcaaggcggcccagtccggggacta
cgggggcgcgggcgacgactacgtgctgggcagcctgcgcgtgagcggctcgggcgg
cggcggcgcgggcaagacggtcaagtgcgtgtttctggatgaggacgacgacgacga
cgacgacgacgagctgcagctgcagatcaaacaggagccggacgaggaggacga
ggaaccaccgcaccagcagctcctgcagccgccggggcagcagccgtcgcagctgct
gagacgctacaacgtcgccaaagtgcccgccagccctacgctgagcagctcggcgga
gtcccccgagggagcgagcctctacgacgaggtgcgggccggcgcgacctcgggcgc
cgggggcggcagccgcctctactacagcttcaagaacatcaccaagcagcacccgcc
gccgctcgcgcagcccgcgctgtcgcccgcgtcctcgcgctcggtgtccacctcctc
gtccagcagcagcggcagcagcagcggcagcagcggcgaggacgccgacgacctgat
gttcgacctgagcttgaatttctctcaaagcgcgcacagcgccagcgagcagcagct
gggggcggcgcggcggccgggaacctgtccctgtcgctggtggataaggatttgga
ttcgttcagcgagggcagcctgggctcccacttcgagttccccgactactgcacgcc
ggagctgagcgagatgatcgcggggactggctggaggcgaacttctccgacctggt
gttcacatattgaaaggcgcccgctgctcgctctttctctcggagggtgcagagctg
ggttccttgggaggaagttgtagtggtgatgatgatgatgataatgatgatgatgat
ggtggtgttgatggtggcggtggtagggtggaggggagagaagaagatgctgatgat
```

*Figure 5*

```
attgataagatgtcgtgacgcaaagaaattggaaaacatgatgaaaattttggtgga
gttaaagtgaaatgagtagtttttaaacattttcctgtcctttttttgtcccccct
cccttcctttatcgtgtctcaaggtagttgcatacctagtctggagttgtgattatt
ttcccaaaaaatgtgttttttgtaattactatttcttttcctgaaattcgtgattgc
aacaaaggcagagggggcggggcggggagggaggtaggacccgctccggaaggcg
ctgtttgaagcttgtcggtctttgaagtctggaagacgtctgcagaggacccttttg
gcagcacaactgttactctagggagttggtggagatatttttttttcttaagagaac
ttaaagaactggtgattttttttaacaaaaaagggaccattgcaacttttgttaa
tttaatttttttttttttttttttttttttttttttggagggagaaaactgatgtc
ttctatgcatccgattcttaacaaaactgcagggagcttgaaaaaatgcagactgta
caaacgcttacaaaaaaaaaactgtgaactgacttaagatcagagtttacttttca
gatcaaattgtttatggttttacaaatgtgatttctacttgccaacttttttttgt
aacttgttcccttatacctccttgattgaataccagacagcctagacctcagtacaa
aaggtattgaaacatttttgatacataacagacctcagtcttttttaaaaattaata
tattttcaggcgtattttttgtacagtgaaaagggaacattcttgctgtgttttttca
gtaagactttcaggcacttcttccctttttgatttctttttttttcctctgtttttttag
catgcaagtatgttggtacgttatgtcctggtttaaaaaggattaaaattttaaaat
aatccttgcatctaaaggccttgtggtttaaaaaaaaaagcaaactttttttttgta
cagctatagtagagatttgttcaatatttgtaggtaaagatttattgaaaatggtga
tatagacctcagagctgttatcttagtttaaagattgtatatgtactgtactatagt
aggactttatgtatctcatacgctgtgatgtggatggggccccagatggaaggtttg
aaactggattctcgattttttagcaaaaagaaaaaaaaaggcacatagtttaaaaa
gtttctcatttttgtgcaatataatctaaataaagtacagaccatctgcatattttgt
agcaaatggtggcaaagcagactcaatgcactgtcgacatcattgcctgttttttt
tttttttttttttgtgctggaagtctgtatcttgacaattttaataaatcagctggaac
tgatagaaactcgcatcgccaatagtctctatggaagtcaaactggaggtcctgttg
tcgcagagcattcggtggtgaggctgttgtgtgcgcggatgaggggaggtggcagga
gagaattctacatttagggggttaggctgaaaagtgttcaattagcaggctgatttc
```

*Figure 5 (cont.)* ttttcctcttccgctagttgtgaaagacaggggaagggtgttctttctctctgccc
tcccttccatctccagctccccatttcctttctcacctcctcctcactccctgcc
tcttctccccacccatcctggcgggcgggctgcgcggaggctcgggagctggccggg
gaggggcggatggagggcctggttgccagctcccttggtcggggtcctgctcgct
ggggcttgtgtgttctctgcggcgggccgcgtcccgctgagcctcgcggtgacagc
cgcctttggcagcgagcgctcggggcacttctatccccgcctctcaaagggtgggga
cagccgtttccagatttgaattttttctgttctttattttaacgctgcatcttcgc
gtgtgctcagaggtggttgttggcggagaacgccgccgcagtgtttgacctctagcg
gtgaaggggaaggggaagaggaaaggagagaagtggtcggtgtctgtttccttctg
tcccccggggccgtggagctgtcggagggaaggaggacggtgcggggccgcaggggg
cgcggggcgcggcgggacccaggctacgagcgggagggaggcgggagtcgggggaag
acgcggcaggccggccgagggcaccccgaggaacatggcatggcctctgtgcgatcc
gagtcgcggtctccggggtgcctgggagggccgaaccactggtgagggcgtggggag
caggggtggcagagggcacccgggcggtagtccgggacgcgcaaggcagagccctg
acgctccgggtccccgtgcctggctcttcttgcctcgccaccgcgtgctcctgggcg
cgccccgccgcgggcccttgaggcgcgcggagacaccagcgctggcttcccgggccc
gcgggccggggagggaagcctcggggctgcggggtgagaggaagaaagcaaacccgg
ggagcaggcggctgccgcacccgcgcaccccgggccctcaccacgccctccccgcgc
gccggctcaggggctgccccggaatcagctccccggggccgccgcaacgaaggtgga
tccgcatcttgattgttctccgggagcctcctgggggctccggcggcggcgcgggcg
cgacccatcccgctggcgctcccgctcgctgaaccccgtttgcctgtccacacccc
ctcgctccccaccatttttcctgaccggcctgtgtccccgagccctcgcggcaggcc
cgagcaggcgatcgcggccgggcacgcgcgccccgggctcccgccccccttccgagc
atccgccgcctcttttctgctgggtctggaggagggaggctgggaggccgctcggg
gcccagcgtgccagccccggagttcagcctcccgagctgcggcgcccgcagcggagg
aggttttcagtggctgattgaaactcactgcaaaatcaccacgactctttcacctac
tgagatgattgaccgaggtttggccttccattttactgagatttggcgagaccgaa
tggaagcgtccgcacagtaactgcagctgctaggccagaggggccccggcgcccttc

```
ccgcctcccctcccgcttgcttttgccttactcgatcttaccaccaccctcccccg
gccccccgactgagaactcgggcctctcacccgcccccagcctcccgctctgggcg
agcctcctcccagccccaccctgggatgcgaagccagcaagcttttgctgcaga
tggacaggtttcttttctgtggcttttcctttcgataaaccatcagatttcagtag
tacatttgggaaaagaagggggctgatggcgttaaccaggttctcaatatagaactgg
atttctggagttgtttaccttaccccacacccctcaacatgtagactaatgcagcc
attggtggtacatttattttagccacggataattgaaccagcggtttacaattgaca
cgtgctccgtgctggtgattttatgtggcagccctctgctgcagttccgaaacttgt
tggcaacgtaaacccattgataggctgatctatgtattttgaaagcctgaaaacttg
gcatgtcttttctgttttaatcatagatgaatcttggacattttctgtggtgaggtg
gaaactttaagtaaattagtaaagtaataatttggcttcagaatgggaagagatagt
caagatttttttttttaaagccatgtggcctaacttgatacaaaataaaagtaat
tgtttggcaatctaaatttaaacctgttagaactcaggacaggcgcttcaatgcgc
ttttttaacaatatttaaggctgttttgatgagtgcgttgtgagaatcatcttaatga
attctttattgagtgtctaaaacatagtataatacacatggtattcttgccactgga
tagtcttcaataaaagtttaattgattttttttgttggtctcttaagtaagtctta
tttttaactaagcattgacagaatatcttaaaatggtaacctgggggtggcgggtgg
gtgctgtgtgcacggcagcctagccagtggggatcctgctgtttattataagtagtt
cacagactctgatggcattttggtaagctttccatctttaagaaattgaaccagcat
tctcttattaattctttaaactgtggaagtaatttccagttcttacactctgatacg
catccttttatttaaaaaaaaaaaaatgctaataaaaggcagtgtacttaaactg
tgctttgcaaatattgtgtatgttatgaatgactacagacactgggcaaattatttg
tagaatgattatcctttagctagagaaagaaatcattacaactcttttgggcagaga
tgtttcttttaatgttaatcaaggggaagtgatttaaatatgcataaatgtagcag
tcagggtgatttagttgcttttttcatgaaagaaaaagactcaaaagacaagactta
tttttctcttctgggacttgaaatcataatcatctgatattagtacagtacaagaaa
tttacatttgttttttacttcagaatttaagtgacttttgcccaaggaatttgagaa
```

Figure 5 (cont.)

```
ataaggcaaataagttgctctattttaaagtagtcattcaatataaatatattatat
caatcttaactttttattctctgatatgattaataatatgtatattcttactttc
ttctaatgggcatatgtatccttgtggacactttgagagagttttcttggactctc
ccatttatagaatctttatactcttttactgtgtggttcctgcttttaacagattt
ctgaggcaaatatatttgtgctttttcttatgtaggaagaccagcgaaaatagttt
actgagttgtcaattttatcagtagataagaaactttctttattacagtttcaggga
agattttttcaggatatttctcagttattctaagggccaaattttgtaaaatttcca
ttaggaatgtcagtttcaaatacctttgtatagcctaagcctgtgaggataacaag
aatgagccttacctatcctaacacagggatttacaagttcccaaagtaaccgtctcc
atgtaactcttgacatacttttctgagatttggcttattttattattggttatttc
tcactgttcattctatttgatttattctacaacatcccctttttatttaatgatctgg
aaaattctgctctttgataacaactcaggattttttgttcagttttggttttgcc
ccttcctgtggagcctacattttcaaccacaataaagatgaaacaaaatttatgaaa
ctgagctctcttccatttacttactgctggctttttttttttttttttccttgat
tcctaccataccttcgttttttcattgtactttttaacactacctatatccatta
gctgcctaattagttttatctgttccatgtggatgcagtgagtttataagagaattt
cacaaacaagtagtttttagtgaacttaaaataaacagaattttaaaggagaccta
tttttatactcaataaaagcacaaagtgcagaaagtataaaacggcttacaaaggg
agacacaagctcataatgttccatgtataaaagtaataactttattgggtagagata
ttcttacaagatctagcacctctgccagtgcacagataggactgttttaaatgattt
gggaacttttggttgcctgcagttgtgaacagagaacttctctacagagaaacaaac
cactaaaagcaatatgaccgagttgagatgtggtttccaatgagcaattggtgaatt
taagcaacctggatgtgcatatgtggaggctcccgtctcactgtttgatcaaacttc
ttttatgtagtcacgtagacttgattttctgctgtgaaaatgaaaaaataaagca
atatgacaaaagtttaaaatgcataaaaataggatttcctctaggctcctcgaa
gagatttttttaatatgatgcttgtcttactttcttagacacgttacatttcccctt
ccaaaaaaaaaaaaaaggacaactggaagtaatttatcatataaagaattttgatca
```

*Figure 5 (cont.)*

```
aatagatattgacaaagggccctctgtcacattttcttcatccagcttttgttcaa
aaacagtatgcctcctcccttgaatcacatagggagaaacgttatactccattctca
ttaatttcccatttttgtctacttttactcttgtacatatgttgtgggtttaagagtc
ttttgcatttgttctgtgaccctttttttgaattgactgttttaaaacggaggcct
atttttttccggtttgggactcctagtggttatggcatcccataatgcttcgtgacgg
ccaccaggacagaaccacctgatgttttagagcagttttcagcatgacactgttaac
aagtgtgtattttccaaggccacatgaaacttactttcttagccactccaggtttgg
gagcagaaaagctgaaaaaccctttttgtgtagaagtctgagtggtttgtggggggga
ccttttttagagtttgcatgccagcgcacggcctattgctgtgaaacagagagaagg
taaagctacctgaggcagtgcgctggaggatgaagtgtttgatagcactaggggga
aagaaaatgcatggcaaagtttcgtcttctcgtagactatctagcatgcagagtgta
gtgtgttgaaacggtgtatgacattgctgtatcaaagttgtaaaattaagcattatt
tattgaaaactatgtattttttgtaaaaacctgatcacatagagaatatcagtggc
ttgtgcttgtgcttcgatctaaccagcttcttgacccaccccccttggtatgcagt
gttaatgctcagggttgaaaatagtacactccaatgtctcttttgcaagagtttttc
acagaggattacatttgttcaaaagactctaataaaattgtgtgatcaatcttcaaa
aaaaaaaaaaaaaaa
```

SEQ ID NO:2

*Figure 5 (cont.)*

SEQUENCE LISTING

```
<160> NUMBER OF SEQ ID NOS: 3

<210> SEQ ID NO 1
<211> LENGTH: 441
<212> TYPE: PRT
<213> ORGANISM: Homo sapiens

<400> SEQUENCE: 1

Met Val Gln Gln Ala Glu Ser Leu Glu Ala Glu Ser Asn Leu Pro Arg
1               5                   10                  15

Glu Ala Leu Asp Thr Glu Glu Gly Glu Phe Met Ala Cys Ser Pro Val
            20                  25                  30

Ala Leu Asp Glu Ser Asp Pro Asp Trp Cys Lys Thr Ala Ser Gly His
        35                  40                  45

Ile Lys Arg Pro Met Asn Ala Phe Met Val Trp Ser Lys Ile Glu Arg
    50                  55                  60

Arg Lys Ile Met Glu Gln Ser Pro Asp Met His Asn Ala Glu Ile Ser
65                  70                  75                  80

Lys Arg Leu Gly Lys Arg Trp Lys Met Leu Lys Asp Ser Glu Lys Ile
                85                  90                  95

Pro Phe Ile Arg Glu Ala Glu Arg Leu Arg Leu Lys His Met Ala Asp
            100                 105                 110

Tyr Pro Asp Tyr Lys Tyr Arg Pro Arg Lys Lys Pro Lys Met Asp Pro
        115                 120                 125

Ser Ala Lys Pro Ser Ala Ser Gln Ser Pro Glu Lys Ser Ala Ala Gly
    130                 135                 140

Gly Gly Gly Gly Ser Ala Gly Gly Gly Ala Gly Gly Ala Lys Thr Ser
145                 150                 155                 160

Lys Gly Ser Ser Lys Lys Cys Gly Lys Leu Lys Ala Pro Ala Ala Ala
                165                 170                 175

Gly Ala Lys Ala Gly Ala Gly Lys Ala Ala Gln Ser Gly Asp Tyr Gly
            180                 185                 190

Gly Ala Gly Asp Asp Tyr Val Leu Gly Ser Leu Arg Val Ser Gly Ser
        195                 200                 205

Gly Gly Gly Gly Ala Gly Lys Thr Val Lys Cys Val Phe Leu Asp Glu
    210                 215                 220

Asp Asp Asp Asp Asp Asp Asp Asp Glu Leu Gln Leu Gln Ile Lys
225                 230                 235                 240
```

Gln Glu Pro Asp Glu Glu Asp Glu Glu Pro Pro His Gln Gln Leu Leu
            245                 250                 255

Gln Pro Pro Gly Gln Gln Pro Ser Gln Leu Leu Arg Arg Tyr Asn Val
        260                 265                 270

Ala Lys Val Pro Ala Ser Pro Thr Leu Ser Ser Ser Ala Glu Ser Pro
    275                 280                 285

Glu Gly Ala Ser Leu Tyr Asp Glu Val Arg Ala Gly Ala Thr Ser Gly
    290                 295                 300

Ala Gly Gly Gly Ser Arg Leu Tyr Tyr Ser Phe Lys Asn Ile Thr Lys
305                 310                 315                 320

Gln His Pro Pro Pro Leu Ala Gln Pro Ala Leu Ser Pro Ala Ser Ser
                325                 330                 335

Arg Ser Val Ser Thr Ser Ser Ser Ser Ser Gly Ser Ser Ser Gly
            340                 345                 350

Ser Ser Gly Glu Asp Ala Asp Asp Leu Met Phe Asp Leu Ser Leu Asn
            355                 360                 365

Phe Ser Gln Ser Ala His Ser Ala Ser Glu Gln Gln Leu Gly Gly Gly
    370                 375                 380

Ala Ala Ala Gly Asn Leu Ser Leu Ser Leu Val Asp Lys Asp Leu Asp
385                 390                 395                 400

Ser Phe Ser Glu Gly Ser Leu Gly Ser His Phe Glu Phe Pro Asp Tyr
                405                 410                 415

Cys Thr Pro Glu Leu Ser Glu Met Ile Ala Gly Asp Trp Leu Glu Ala
                420                 425                 430

Asn Phe Ser Asp Leu Val Phe Thr Tyr
            435                 440

<210> SEQ ID NO 2
<211> LENGTH: 8737
<212> TYPE: DNA
<213> ORGANISM: Homo sapiens

<400> SEQUENCE: 2

```
acctccgcac gagacccagc ggcccgggtt ggagcgtcca gccctgcagc ggatcatggt     60
gcagcaggcg gagagcttgg aagcggagag caacctgccc cgggaggcgc tggacacgga    120
ggagggcgaa ttcatggctt gcagcccggt ggccctggac gagagcgacc agactggtg    180
caagacggcg tcgggccaca tcaagcggcc gatgaacgcg ttcatggtat ggtccaagat    240
cgaacgcagg aagatcatgg agcagtctcc ggacatgcac aacgccgaga tctccaagag    300
gctgggcaag cgctggaaaa tgctgaagga cagcgagaag atcccgttca tccgggaggc    360
ggagcggctg cggctcaagc acatggccga ctaccccgac tacaagtacc ggccccggaa    420
aaagcccaaa atggacccct cggccaagcc cagcgccagc cagagcccag agaagagcgc    480
ggccggcggc ggcggcggga gcgggcggcg aggcgcgggc ggtgccaaga cctccaaggg    540
ctccagcaag aaatgcggca gctcaaggc ccccgcggcc gcgggcgcca aggcgggcgc    600
gggcaaggcg gcccagtccg gggactacgg gggcgcgggc gacgactacg tgctgggcag    660
cctgcgcgtg agcggctcgg gcggcggcgg cgcgggcaag acggtcaagt gcgtgttctc    720
ggatgaggac gacgacgacg acgacgacga cgacgagctg cagctgcaga tcaaacagga    780
gccggacgag gaggacgagg aaccaccgca ccagcagctc ctgcagccgc ggggcagca    840
gccgtcgcag ctgctgagac gctacaacgt cgccaaagtg cccgccagcc ctacgctgag    900
cagctcggcg gagtcccccg agggagcgag cctctacgac gaggtgcggg ccggcgcgac    960
```

```
ctcgggcgcc gggggcggca gccgcctcta ctacagcttc aagaacatca ccaagcagca    1020
cccgccgccg ctcgcgcagc ccgcgctgtc gcccgcgtcc tcgcgctcgg tgtccacctc    1080
ctcgtccagc agcagcggca gcagcagcgg cagcagcggc gaggacgccg acgacctgat    1140
gttcgacctg agcttgaatt tctctcaaag cgcgcacagc gccagcgagc agcagctggg    1200
gggcggcgcg gcggccggga acctgtccct gtcgctggtg gataaggatt tggattcgtt    1260
cagcgagggc agcctgggct cccacttcga gttccccgac tactgcacgc cggagctgag    1320
cgagatgatc gcgggggact ggctggaggc gaacttctcc gacctggtgt tcacatattg    1380
aaaggcgccc gctgctcgct ctttctctcg gagggtgcag agctgggttc cttgggagga    1440
agttgtagtg gtgatgatga tgatgataat gatgatgatg atggtggtgt tgatggtggc    1500
ggtggtaggg tggaggggag agaagaagat gctgatgata ttgataagat gtcgtgacgc    1560
aaagaaattg gaaaacatga tgaaaatttt ggtggagtta aagtgaaatg agtagttttt    1620
aaacattttt cctgtccttt ttttgtcccc cctcccttcc tttatcgtgt ctcaaggtag    1680
ttgcatacct agtctggagt tgtgattatt ttcccaaaaa atgtgttttt gtaattacta    1740 tttcttttc ctgaaattcg tgattgcaac aaaggcagag ggggcgggc ggggagggg    1800 aggtaggacc cgctccggaa ggcgctgttt gaagcttgtc ggtctttgaa gtctggaaga    1860
cgtctgcaga ggacccttt ggcagcacaa ctgttactct agggagttgg tggagatatt    1920
tttttttctt aagagaactt aaagaactgg tgatttttt ttaacaaaaa aagggaccat    1980
tgcaactttt gttaatttaa tttttttttt tttttttttt tttttttttt ttggagggag    2040
aaaactgatg tcttctatgc atccgattct taacaaaact gcagggagct tgaaaaaatg    2100
cagactgtac aaacgcttac aaaaaaaaaa actgtgaact gacttaagat cagagtttac    2160
ttttcagatc aaattgttta tggttttaca aatgtgattt ctacttgcca acttttttt    2220 tgtaacttgt tcccttatac ctccttgatt gaataccaga cagcctagac ctcagtacaa    2280
aaggtattga acattttg atacataaca gacctcagtc tttttaaaa attaatatat    2340 tttcaggcgt atttttgtac agtgaaaagg gaacattctt gctgtgtttt ttcagtaaga    2400
ctttcaggca cttcttccct tttgatttct ttttttcct ctgtttttta gcatgcaagt    2460
atgttggtac gttatgtcct ggtttaaaaa ggattaaaat tttaaaataa tccttgcatc    2520
taaaggcctt gtggtttaaa aaaaaaagc aaacttttt ttgtacagct atagtagaga    2580
tttgttcaat atttgtaggt aaagatttat tgaaaatggt gatatagacc tcagagctgt    2640
tatcttagtt taaagattgt atatgtactg tactatagta ggactttatg tatctcatac    2700
gctgtgatgt ggatggggcc ccagatggaa ggtttgaaac tggattctcg attttagca    2760 aaaagaaaa aaaaaggca catagtttaa aaagtttctc attttgtgca atataatcta    2820
aataaagtac agaccatctg catattttgt agcaaatggt ggcaaagcag actcaatgca    2880
ctgtcgacat cattgcctgt tttttttttt ttttttgt gctggaagtc tgtatcttga    2940 caatttaat aaatcagctg gaactgatag aaactcgcat cgccaatagt ctctatggaa    3000
gtcaaactgg aggtcctgtt gtcgcagagc attcggtggt gaggctgttg tgtgcgcgga    3060
tgaggggagg tggcaggaga gaattctaca tttaggggg taggctgaaa agtgttcaat    3120
tagcaggctg atttctttt cctcttccgc tagttgtgaa agacagggga agggtgttct    3180
ttctctctgc cctcccttc catctccagc tccccatttc cttctcacc tcctcctcca    3240 ctccctgcct cttctcccca cccatcctgg cgggcgggct gcgcggaggc tcgggagctg    3300
```

-continued

```
gccggggagg ggcggatgga ggggcctggg ttgccagctc ccttggtcgg ggtcctgctc     3360 gctgggctt gtgtgttctc tgcggcgggc cgcgtcccg ctgagcctcg cggtgacagc       3420
cgcctttggc agcgagcgct cggggcactt ctatccccgc ctctcaaagg gtggggacag    3480
ccgtttccag atttgaattt tttctgttct ttatttttaa cgctgcatct tcgcgtgtgc    3540
tcagaggtgg ttgttggcgg agaacgccgc cgcagtgttt gacctctagc ggtgaagggg   3600
gaaggggaag aggaaaggag agaagtggtc ggtgtctgtt tccttctgtc ccccggggcc    3660
gtggagctgt cggagggaag gaggacggtg cggggccgca gggggcgcgg ggcgcggcgg   3720
gacccaggct acgagcggga gggaggcggg agtcggggga agacgcggca ggccggccga   3780 gggcacccg aggaacatgg catggcctct gtgcgatccg agtcgcggtc tccggggtgc    3840
ctgggagggc cgaaccactg gtgagggcgt ggggagcagg gggtggcaga gggcacccgg    3900
gcggtagtcc gggacgcgca aggcagagcc ctgacgctcc gggtccccgt gcctggctct   3960
tcttgcctcg ccaccgcgtg ctcctgggcg cgccccgccg cgggcccttg aggcgcgcgg   4020
agacaccagc gctggcttcc cgggcccgcg ggccggggag ggaagcctcg gggctgcggg   4080
gtgagaggaa gaaagcaaac ccggggagca ggcggctgcc gcaccgcgc accccgggcc    4140 ctcaccacgc cctccccgcg cgccggctca ggggctgccc cggaatcagc tccccggggc   4200
cgccgcaacg aaggtggatc cgcatcttga ttgttctccg ggagcctcct gggggctccg   4260
gcggcggcgc gggcgcgacc catcccgctg gcgctcccg ctcgctgaac cccgtttgcc    4320
tgtccacacc ccctcgctcc ccaccatttt tcctgaccgg cctgtgtccc cgagccctcg   4380
cggcaggccc gagcaggcga tcgcggccgg gcacgcgcgc cccgggctcc cgccccccctt  4440 ccgagcatcc gccgcctctt ttctgctggg tctgggagga gggaggctgg gaggccgctc    4500
ggggcccagc gtgccagccc cggagttcag cctcccgagc tgcggcgccc gcagcggagg   4560
aggttttcag tggctgattg aaactcactg caaaatcacc acgactcttt cacctactga    4620
gatgattgac cgaggtttgg ccttccattt ttactgagat ttggcgagac cgaatgaag   4680 cgtccgcaca gtaactgcag ctgctaggcc agaggggccc cggcgccctt cccgcctccc    4740
ctcccgcttg cttttgcctt actcgatctt accaccaccc ctcccccggc ccccccgactg   4800 agaactcggg cctctcaccc gccccccagc ctcccgctct gggcgagcct cctccccagc    4860 ccccaccct gggatgcgaa gccagcaagc ttttgctgca gatggacagg tttcttttct     4920 gtggctttt cctttcgata aaccatcaga tttcagtagt acatttggga aaagaagggg     4980
ctgatggcgt taaccaggtt ctcaatatag aactggattt ctggagttgt ttaccttacc   5040 ccacacccc tcaacatgta gactaatgca gccattggtg gtacatttat tttagccacg    5100
gataattgaa ccagcggttt acaattgaca cgtgctccgt gctggtgatt ttatgtggca   5160
gccctctgct gcagttccga aacttgttgg caacgtaaac ccattgatag gctgatctat    5220
gtattttgaa agcctgaaaa cttggcatgt cttttctgtt ttaatcatag atgaatcttg    5280
gacattttct gtggtgaggt ggaaacttta agtaaattag taaagtaata atttggcttc    5340
agaatgggaa gagatagtca agattttttt tttttaaagc catgtggcct aacttgatac    5400
aaaaataaaa gtaattgttt ggcaatctaa atttaaaacc tgttagaact caggacaggc    5460
gcttcaatgc gcttttaac aatatttaag gctgttttga tgagtgcgtt gtgagaatca    5520
tcttaatgaa ttcttttattg agtgtctaaa acatagtata atacacatgg tattcttgcc   5580 actgatagt cttcaataaa agtttaattg atttttttt gttggtctct taagtaagtc     5640
ttatttttaa ctaagcattg acagaatatc ttaaaatggt aacctggggg tggcgggtgg   5700
```

```
gtgctgtgtg cacggcagcc tagccagtgg ggatcctgct gtttattata agtagttcac   5760
agactctgat ggcattttgg taagcttttcc atctttaaga aattgaacca gcattctctt   5820
attaattctt taaactgtgg aagtaatttc cagttcttac actctgatac gcatccctttt  5880 tatttaaaaa aaaaaaaaat gctaataaaa ggcagtgtac ttaaactgtg ctttgcaaat   5940
attgtgtatg ttatgaatga ctacagacac tgggcaaatt atttgtagaa tgattatcct   6000
ttagctagag aaagaaatca ttacaactct tttgggcaga gatgtttctt tttaatgtta   6060
atcaagggga agtgatttaa atatgcataa atgtagcagt cagggtgatt tagttgcttt   6120
tttcatgaaa gaaaaagact caaaagacaa gacttatttt tctcttctgg gacttgaaat   6180
cataatcatc tgatattagt acagtacaag aaatttacat ttgttttta cttcagaatt    6240 taagtgactt tgcccaagg aatttgagaa ataaggcaaa taagttgctc tattttaaag    6300
tagtcattca atataaatat attatatcaa tcttaacttt tttattctct gatatgatta   6360
ataatatgta tattcttact tttcttctaa tgggcatatg tatccttgtg gacactttga   6420
gagaggtttt cttggactct cccatttata gaatctttat actctttttac tgtgtggttc   6480 cctgctttta acagatttct gaggcaaata tatttgtgct tttttcttat gtaggaagac   6540
cagcgaaaat agtttactga gttgtcaatt ttatcagtag ataagaaact ttcttattat   6600
cagtttcagg gaagattttt tcaggatatt tctcagttat tctaagggcc aaattttgta   6660
aaatttccat taggaatgtc agtttcaaat acccctttgta tagcctaagc ctgtgaggat   6720
aacaagaatg agccttacct atcctaacac agggatttac aagttcccaa agtaaccgtc   6780
tccatgtaac tcttgacata ctttttctgag atttggctta ttttttattat tggttatttc   6840 tcactgttca ttctatttga tttattctac aacatcccct tttatttaat gatctggaaa   6900
attctgctct ttgataacaa ctcaggattt ttttgttcag ttttggtttt tgccccttcc    6960
tgtggagcct acattttcaa ccacaataaa gatgaaacaa aatttatgaa actgagctct   7020
cttccatttt acttactgct ggcttttttt tttttttttt tccttgattc ctaccatacc   7080
ttcgtttttt tcattgtact ttttttaacac tacctatatc cattagctgc ctaattagtt   7140
ttatctgttc catgtggatg cagtgagttt ataagagaat ttcacaaaca agtagttttt   7200
tagtgaactt aaaataaaca gaattttaaa ggagacctat ttttatactc aataaaagca   7260
caaaagtgca gaaagtataa aacggcttac aaagggagac acaagctcat aatgttccat   7320
gtataaaagt aataacttta ttgggtagag atattcttac aagatctagc acctctgcca   7380
gtgcacagat aggactgttt taaatgattt gggaactttt ggttgcctgc agttgtgaac   7440
agagaacttc tctacagaga aacaaaccac taaaagcaat atgaccgagt tgagatgtgg   7500
tttccaatga gcaattggtg aatttaagca acctggatgt gcatatgtgg aggctcccgt   7560
ctcactgttt gatcaaactt cttttatgta gtcacgtaga cttgattttt tctgctgtga   7620
aaatgaaaaa ataagcaat atgacaaaaa gtttaaaaat gcataaaaaa taggatttcc    7680
tctaggctcc tcgaagagat ttttttaata tgatgcttgt cttactttct tagacacgtt   7740
acatttcccc ttccaaaaaa aaaaaaaagg acaactggaa gtaatttatc atataaagaa   7800
ttttgatcaa atagatattg acaaagggcc ctctgtcaca ttttttcttca tccagctttt   7860 gttcaaaaac agtatgcctc ctcccttgaa tcacataggg agaaacgtta tactccattc   7920
tcattaattt cccatttgt ctactttac tcttgtacat atgttgtggg tttaagagtc      7980
ttttgcattt gttctgtgac acctttttttt gaattgactg ttttaaaacg gaggcctatt   8040
```

```
ttttccggtt tgggactcct agtggttatg gcatcccata atgcttcgtg acggccacca    8100
ggacagaacc acctgatgtt ttagagcagt tttcagcatg acactgttaa caagtgtgta    8160
ttttccaagg ccacatgaaa cttactttct tagccactcc aggtttggga gcagaaaagc    8220
tgaaaaaccc ttttgtgtag aagtctgagt ggtttgtggg ggggaccttt tttagagttt    8280
gcatgccagc gcacggccta ttgctgtgaa acagagagaa ggtaaagcta cctgaggcag    8340
tgcgctggag gatgaagtgt ttgatagcac tagggggggaa agaaaatgca tggcaaagtt    8400
tcgtcttctc gtagactatc tagcatgcag agtgtagtgt gttgaaacgg tgtatgacat    8460
tgctgtatca aagttgtaaa attaagcatt atttattgaa aactatgtat tttttttgtaa   8520 aaacctgatc acatagagaa tatcagtggc ttgtgcttgt gcttcgatct aaccagcttc    8580
ttgacccacc ccccttggt atgcagtgtt aatgctcagg gttgaaaata gtacactcca     8640
atgtctcttt tgcaagagtt tttcacagag gattacattt gttcaaaaga ctctaataaa    8700
attgtgtgat caatcttcaa aaaaaaaaaa aaaaaa                              8737

<210> SEQ ID NO 3
<211> LENGTH: 111
<212> TYPE: PRT
<213> ORGANISM: Homo sapiens

<400> SEQUENCE: 3

Phe Met Val Trp Ser Lys Ile Glu Arg Arg Lys Ile Met Glu Gln Ser
1               5                  10                  15

Pro Asp Met His Asn Ala Glu Ile Ser Lys Arg Leu Gly Lys Arg Trp
            20                  25                  30

Lys Met Leu Lys Asp Ser Glu Lys Ile Pro Phe Ile Arg Glu Ala Glu
        35                  40                  45

Arg Leu Arg Leu Lys His Met Ala Asp Tyr Pro Asp Tyr Lys Tyr Arg
    50                  55                  60

Pro Arg Lys Lys Pro Lys Met Asp Pro Ser Ala Lys Pro Ser Ala Ser
65                  70                  75                  80

Gln Ser Pro Glu Lys Ser Ala Ala Gly Gly Gly Gly Ser Ala Gly
                85                  90                  95

Gly Gly Ala Gly Gly Ala Lys Thr Ser Lys Gly Ser Ser Lys Lys
            100                 105                 110
```

SOX11 EXPRESSION IN MALIGNANT LYMPHOMAS

The present application is §371 application of PCT/GB2008/001625 filed May 12, 2008 which claims priority to GB Patent Application No. 0709092.1 filed May 11, 2007, the entire disclosure of each being incorporated by reference herein.

FIELD OF INVENTION

The present invention relates to the transcription factor Sox11 and use of binding agents which bind thereto in the imaging and/or diagnosis of lymphomas, for example mantle cell lymphoma (MCL) and diffuse large B-cell lymphoma (DLBCL).

INTRODUCTION

The term lymphoma refers to all the malignancies of the lymphocytes, with B and T cell malignancies being the most commonplace. The classification of lymphomas is still under debate and far from conclusive. The current classification being used is the Revised European American Classification of Lymphomas (Harris et al., 1994, *Blood* 84:1361-1392). However, this system needs to be further divided to allow as precise diagnosis as possible, thereby permitting the optimal treatment for the patients.

B cell lymphomas are malignancies of B lymphocytes and can be divided into several subgroups depending on their morphological and phenotypic properties, according to the WHO classification (Harris et al., 2000, *Pathol* 13: 193-207). The main groups of B cell neoplasms are precursor B-lymphoblastic leukemia/lymphoma, chronic lymphocytic leukemia/lymphoma (CLL), plasma cell myeloma, extra nodal marginal zone B cell lymphoma of mucosa-associated lymphoid tissue type, follicular lymphoma (FL), mantle cell lymphoma (MCL), diffuse large B cell lymphoma and Burkitt lymphoma (Harris et al., 2000, *Pathol* 13: 193-207).

Several gene expression studies of different types of B-cell lymphomas have been published. For example, Golub et al., 1999 *Science* 286:531-537 have shown that acute myeloid leukaemia (AML) and acute lymphoblastic leukaemia (ALL) can be distinguished based on their gene expression analysis. In addition, Alizadeh et al., 2000 *Nature* 403:503-511 found two distinct types of diffuse large B-cell lymphoma (DLBCL) when analysing the gene expression of these tumours on the Lymphochip.

B-cells go through several differentiation stages during development. The immature B-cell migrates from bone-marrow to the lymph node where the naïve B-cell is stimulated to migrate into the B-cell follicles, forming Germinal Centres, before finally differentiating into an antibody secreting plasma cell. For each of these different stages a malignant counterpart has been found that resembles the normal B-cell origin (Pascual et al., 1997, *Baillieres Clin Haematol* 10:525-538).

Mantle cell lymphomas (MCLs) are believed to derive from a naïve B-cell, although the relationship with the CD5$^+$ B-1 cells also has been discussed (Pascual et al., supra; Capello et al., 2000, *Haematologica* 85:195-201). MCLs are indolent and show no somatic mutation of their immunoglobulin genes, thus resembling their naïve B-cell origin. The median age of disorder for MCL patients is 60 years and the median survival is 2 to 5 years with a poor response to conventional therapeutic regimens (Weisenburger et al., 2000, *Am J Hematol* 64:190-196). Seventy percent of the patients have bone marrow involvement and the male to female predominance is 3:1 (Kurtin, 1998, *Adv Anat Pathol* 5:376-398). MCL cells express the pan-B-cell markers CD5, CD19, CD20, CD22, CD79a and CD79b and are negative for CD10 and CD23 (Kurtin, 1998, *Adv Anat Pathol* 5:376-398). MCL tumours can grow in three different growth patterns, mantle zone, nodular and diffuse pattern. There are also several morphological variants with different median survival (monocytoid B-cell like, pleomorphic or anaplastic variant, large cell variant and blastoid variant) that fill the criteria for being designated as MCLs (CD20$^+$ neoplasms that are CD43$^+$, CD5$^+$, CD23$^-$, CD10$^-$ and cyclin D1 positive) (Kurtin, 1998, *Adv Anat Pathol* 5:376-398). Follicular dendritic cell meshwork positive for CD21, CD23 and CD35 can often be seen in the MCL tumour tissue (Kurtin, 1998, *Adv Anat Pathol* 5:376-398).

The sub-grouping of B cell lymphomas is necessary for the decision of therapeutic strategy as different types of lymphomas are known to respond differentially to various treatments. Thus, the possibility to accurate diagnosis different lymphomas in a robust and simple manner is crucial for the ability to promptly start treating the patient accordingly.

Today MCL are separated from chronic lymphocytic leukemia/lymphoma and follicular lymphoma based on the expression of CD23 and CD10, which are generally negative in MCL but positive in chronic lymphocytic leukemia/lymphoma and follicular lymphoma, respectively. Furthermore, the overexpression of cyclin D1, the hallmark of MCL, is used to diagnosis MCL and separates it from other malignancies.

However, some MCL show the characteristic translocation t(11; 14) that puts the BCL1 gene (cyclin D1) under the control of the immunoglobulin heavy chain promoter but lack expression of the protein (Stacey et al., 2003, *Curr Opin Cell Biol* 15: 158-63; Donnellan et al., 1998, *Mol Pathol* 51: 1-7). The opposite situation where the protein is detected but the translocation cannot be confirmed is also common due to the heterogeneity of the translocation break-point region. Cyclin D1 promotes the G1 to S phase transition and is believed to be one of the main features contributing to the malignant behaviour of MCL.

MCL is recognised as one of the most severe forms of lymphoma, generally exhibiting a resistance to conventional chemotherapy and a rapid clinical progression in many cases to incurable malignancies with a median survival time of 3 years (Kurtin 1998 supra).

Diffuse large B cell lymphoma (DLBCL) is a heterogeneous entity and only curable in less than 50% of patients. The international prognosis (IPI) index is used to predict outcome for patients according to clinical parameters, such as elevated LDH, number of extranodal sites and stage but also including performance status and age as a risk factor. Molecular marker with biological relevance and prognostic use has been sought and both bcl-2 and bcl-6 have shown to be correlated to survival. However, it was recently shown that for patients treated with R-CHOP (combination therapy with CHOP and Retuximab) those markers are no longer useful. A revised version of IPI remains the only prognostic marker for DLBCL treated with R-CHOP.

Hence, there is also a need for improved methods of diagnosing and prognosing lymphomas, such as mantle cell lymphomas (MCL) and diffuse large B-cell lymphoma (DLBCL).

SUMMARY OF INVENTION

The first aspect of the invention provides a binding moiety which is capable of binding selectively to Sox11 protein, or to a nucleic acid molecule encoding the same, for diagnosing or prognosing a lymphoma.

Thus, it will be appreciated that the invention also provides the use of a binding moiety which is capable of binding selectively to Sox11 protein, or to a nucleic acid molecule encoding the same, in the preparation of a diagnostic or prognostic agent for mantle cell lymphoma.

In one embodiment, the lymphoma is a mantle cell lymphoma (MCL). For example, the binding moiety may be for diagnosing MCL.

In a further embodiment, the lymphoma is a diffuse large B-cell lymphoma (DLBCL). For example, the binding moiety may be for prognosing DLBCL.

SOX11 belongs to the Sox gene family and proteins are grouped into this family if they contain a DNA-binding HMG-domain (High Mobility Group) with strong amino acid similarity (usually >50%) to the HMG domain of Sry, a sex-determining protein (Wegner, 1999, *Nucleic Acids Res* 27: 1409-20). More than 20 Sox gene family members have been identified in different species and grouped into 7 subgroups according to the homology within and outside the HMG-domain. The human Sox11 belong to the subgroup C and is homologous to Sox4 with 55% identity on the amino acid level within the C-terminal transactivation domain and 86% identity for the HMG-domain (Wegner, 1999, *Nucleic Acids Res* 27: 1409-20). Sox11 and Sox4 have also been shown to display complementary roles in the developing nervous system (Cheung et al., 2000, *Brain Res Mol Brain Res* 79: 180-91). While Sox4 has been shown to be crucial for B lymphopoiesis (Smith and Sigvardsson, 2004, *J Leukoc Biol* 75: 973-81), there is no previous report on Sox11 expression in neither normal nor malignant B cells.

Hence, by "Sox11 protein" we include the amino acid sequence of the human Sox11 protein as shown in FIG. 4 herein, as well as naturally-occurring homologues thereof.

The present inventors have surprisingly identified Sox11 as a diagnostic antigen for lymphomas, such as MCL, using immunohistochemistry analysis. Not only is this is the first report showing expression of Sox11 in cells of the B cell lineage, the differential localization and the intensity of the staining differentiate MCL from non-malignant tonsil B cells but also from other types of lymphomas as chronic lymphocytic leukemia/lymphoma, follicular lymphoma and diffuse large B-cell lymphoma. Thus, Sox11 provides a valuable marker for diagnosing MCL patients and facilitates accurate diagnosis of this aggressive malignancy.

By "diagnosing" we include the act or process of identifying the existence and type of a lymphoma from which an individual may be suffering. Thus, in one embodiment, diagnosis includes the differentiation of a particular lymphoma type, such as MCL or DLBCL, from one or more other lymphomas.

By "prognosis" we include the act or process of predicting the probable course and outcome of a lymphoma, e.g. determining survival probability.

By "binding moiety" it is meant a molecule or segment of a molecule which is capable of binding to another molecule or molecules.

It will be appreciated by persons skilled in the art that the binding moieties of the invention may be used in vivo or in vitro.

In one embodiment, the binding moiety of the invention is for use in the detection of Sox11 expression as a sole biomarker for lymphoma. For example, Sox11 expression may be used as a sole biomarker for the differentiation of a particular lymphoma type, such as MCL or DLBCL, from one or more other lymphomas. Alternatively, or in addition, the Sox11 expression may be used as a sole biomarker for the prognosis of a lymphoma, such as DLBCL.

Alternatively, the binding moiety of the invention may be for use in combination with one or more additional binding moieties for detecting one or more additional biomarkers for lymphoma. Thus, the binding moiety may be for use in combination with fewer than 20 additional binding moieties, for example fewer than 15, 10, 8, 6, 5, 4, 3, 2 or 1 additional binding moieties.

In one particular embodiment, the binding moiety of the invention is for detecting nuclear expression of Sox11.

By "binding selectively" we include binding moieties which bind more strongly to Sox11 than to another polypeptides or nucleic acids; preferably at least 10-fold more strongly, more preferably at least 50-fold more strongly and even more preferably, at least 100-fold more strongly. Preferably, the binding moieties bind only to Sox11 polypeptides or nucleic acids.

The term 'polypeptide' as used herein means a plurality of amino acids that are linked together via a peptide bond. The term 'peptide' may be used interchangeably with the term 'polypeptide' however a peptide may be composed of two or more polypeptides.

The term 'amino acid' as used herein includes the standard twenty genetically-encoded amino acids and their corresponding stereoisomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids.

When an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

The nucleic acid molecule of the invention may be DNA, RNA or PNA and preferably DNA. The nucleic acid molecule may or may not contain introns in the coding sequence; preferably the nucleic acid molecule is a cDNA.

Thus, the isolated nucleic acid molecule is suitable for expressing a polypeptide of the invention. By 'suitable for expressing' is meant that the nucleic acid molecule is a polynucleotide that may be translated to form the polypeptide, for example RNA, or that the polynucleotide (which is preferably DNA) encoding the polypeptide of the invention is inserted into an expression vector, such as a plasmid, in proper orientation and correct reading frame for expression. The polynucleotide may be linked to the appropriate transcriptional and translational regulatory control nucleotide sequences recognised by any desired host; such controls may be incorporated in the expression vector.

Generally, the nucleic acid molecule is inserted into an expression vector, such as a plasmid, in proper orientation and correct reading frame for expression. If necessary, the nucleic acid molecule may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a polynucleotide sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant nucleic acid molecule of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, mammal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith. Promoter sequences compatible with exemplary bacterial hosts are typically provided in plasmid vectors containing convenient restriction sites for insertion of a polynucleotide of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors.

Transformation of appropriate cell hosts with a nucleic acid molecule of the present invention is accomplished by well known methods that typically depend on the type of vector used. With regard to transformation of prokaryotic host cells, see for example Sambrook & Russell (Sambrook and Russell, 2001, *Molecular Cloning, A Laboratory Manual*, 3$^{rd}$ edition, Cold Spring Harbor Laboratory, Cold Spring Harbor, N.Y.). Transformation of yeast cells is described in numerous reviews, for example see Gietz & Woods (2001) *Biotechniques* 30:816-228. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells. For example, many bacterial species may be transformed by the methods described in Luchansky et al. (1988) *Mol. Microbiol.* 2:637-646. Methods for transformation of yeast by electroporation are disclosed in Becker & Guarente (1990) *Methods Enzymol.* 194:182.

Successfully transformed cells, i.e. cells that contain a nucleic acid molecule of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Sambrook & Russell (supra.). Alternatively, the presence of the protein in the supernatant can be detected using antibodies.

In addition to assaying directly for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

The second aspect of the invention provides a binding moiety which is capable of binding selectively to Sox11 protein, or to a nucleic acid molecule encoding the same, for detecting lymphoma cells in a sample (for example MCL or DLBCL).

One embodiment of the invention provides the use according to either the first or second aspect wherein the binding moiety is capable of binding selectively to Sox11 protein.

Conveniently the binding moiety is capable of binding selectively to a polypeptide comprising an amino acid sequence of SEQ ID NO:1 (see FIG. 4) and/or natural variants thereof.

By "natural variants" we include, for example, allelic variants. Typically, these will vary from the given sequence by only one or two or three, and typically no more than 10 or 20 amino acid residues. Typically, the variants have conservative substitutions.

Variants of polypeptides include polypeptides comprising a sequence with at least 60% identity to known amino acid sequences, preferably at least 70% or 80% or 85% or 90% identity to said sequences, and more preferably at least 95%, 96%, 97%, 98% or 99% identity to said amino acid sequences.

Percent identity can be determined by, for example, the LALIGN program (Huang and Miller, *Adv. Appl. Math.* (1991) 12:337-357) at the Expasy facility site (http://www.ch.embnet.org/software/LALIGN_form.html) using as parameters the global alignment option, scoring matrix BLOSUM62, opening gap penalty −14, extending gap penalty −4. Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

Preferably the binding moiety comprises or consists of a polypeptide.

Polypeptide binding moieties can be identified by means of a screen. A suitable method or screen for identifying peptides or other molecules which selectively bind a target protein or polypeptide may comprise contacting the target protein or polypeptide with a test peptide or other molecule under conditions where binding can occur, and then determining if the test molecule or peptide has bound the target protein or peptide. Methods of detecting binding between two moieties are well known in the art of biochemistry. Preferably, the known technique of phage display is used to identify peptides or other ligand molecules suitable for use as binding moieties. An alternative method includes the yeast two hybrid system.

More preferably the binding moiety comprises or consists of an antibody, or an antigen-binding fragment or variant thereof.

By "antibody" we include not only whole immunoglobulin molecules but also fragments thereof such as Fab, F(ab')$_2$, Fv and other fragments thereof that retain the antigen-binding site. Similarly the term "antibody" includes genetically engineered derivatives of antibodies such as single chain Fv molecules (scFv) and single domain antibodies (dAbs). The term also includes antibody-like molecules which may be produced using phage-display techniques or other random selection techniques.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al, 1984, *Proc. Natl. Acad. Sci. USA* 81:6851-6855).

That antigenic specificity is conferred by variable domains and is independent of the constant domains is known from experiments involving the bacterial expression of antibody fragments, all containing one or more variable domains. These molecules include Fab-like molecules (Better et al, 1988, *Science* 240: 1041); Fv molecules (Skerra et al, 1988, *Science* 240:1038); single-chain Fv (ScFv) molecules where the $V_H$ and $V_L$ partner domains are linked via a flexible oligopeptide (Bird et al, 1988, *Science* 242:423; Huston et al., 1988, *Proc. Natl. Acad. Sci. USA* 85:5879) and single domain antibodies (dAbs) comprising isolated V domains (Ward et al., 1989, *Nature* 341:544). A general review of the techniques involved in the synthesis of antibody fragments which retain their specific binding sites is to be found in Winter & Milstein, 1991, *Nature* 349:293-299.

By "ScFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration to the target site. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site.

Although the antibody may be a polyclonal antibody, it is preferred if it is a monoclonal antibody. In some circumstances, particularly if the antibody is going to be administered repeatedly to a human patient, it is preferred if the monoclonal antibody is a human monoclonal antibody or a humanised monoclonal antibody.

Suitable monoclonal antibodies may be prepared by known techniques, for example those disclosed in "*Monoclonal Antibodies; A manual of techniques*", H Zola (CRC Press, 1988) and in "*Monoclonal Hybridoma Antibodies: Techniques and Application*", S G R Hurrell (CRC Press, 1982). Polyclonal antibodies may be produced which are polyspecific or monospecific. It is preferred that they are monospecific.

Chimaeric antibodies are discussed by Neuberger et al (1998, 8$^{th}$ *International Biotechnology Symposium* Part 2, 792-799).

Suitably prepared non-human antibodies can be "humanised" in known ways, for example by inserting the CDR regions of mouse antibodies into the framework of human antibodies.

The antibodies may be human antibodies in the sense that they have the amino acid sequence of human antibodies with specificity for one of the proteins identified in Table 1 but they may be prepared using methods known in the art that do not require immunisation of humans. For example, transgenic mice are available which contain, in essence, human immunoglobulin genes (see Vaughan et al., 1998, *Nature Biotechnol* 16:535-539.

Thus, in a preferred embodiment of the invention the antibody or antigen-binding fragment or variant thereof is selected from the group consisting of Fv fragments, Fab-like fragments, single variable domains and domain antibodies.

A further preferred embodiment of the invention is a use wherein the antibody or an antigen-binding fragment or variant thereof is humanised.

A further embodiment of the present invention provides a use according to any one of aspects one or two wherein the binding moiety is capable of binding selectively to a nucleic acid molecule encoding Sox11 protein.

Preferably the binding moiety is capable of binding selectively to a nucleic acid molecule encoding a polypeptide comprising an amino acid sequence of SEQ ID NO:1 and/or natural variants thereof.

More preferably the binding moiety comprises or consists of a nucleic acid molecule. Even more preferably the binding moiety comprises or consists of a DNA molecule. Advantageously the binding moiety comprises or consists of a fragment of the nucleotide sequence of SEQ ID NO:2 (see FIG. 5), or fragment or a variant thereof. Conveniently the invention the nucleic acid molecule is 5 to 100 nucleotides in length. More conveniently the nucleic acid molecule is 15 to 35 nucleotides in length. Preferably the binding moiety comprises a detectable moiety.

By a "detectable moiety" we include the meaning that the moiety is one which, when located at the target site following administration of the compound of the invention into a patient, may be detected, typically non-invasively from outside the body and the site of the target located. Thus, the compounds of this embodiment of the invention are useful in imaging and diagnosis.

Typically, the detectable moiety is or comprises a radioactive atom which is useful in imaging. Suitable radioactive atoms include $^{99m}$Tc and $^{123}$I for scintigraphic studies. Other readily detectable moieties include, for example, spin labels for magnetic resonance imaging (MRI) such as $^{123}$I again, $^{131}$I, $^{111}$In, $^{19}$F, $^{13}$C, $^{15}$N, $^{17}$O, gadolinium, manganese or iron. Clearly, the compound of the invention must have sufficient of the appropriate atomic isotopes in order for the molecule to be readily detectable.

The radio- or other labels may be incorporated in the compound of the invention in known ways. For example, if the binding moiety is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker et al., 1978, *Biochem. Biophys. Res. Comm.* 80:49-57) can be used to incorporate $^{123}$I. Reference ("Monoclonal Antibodies in Immunoscintigraphy", J-F Chatal, CRC Press, 1989) describes other methods in detail.

Thus, in a further embodiment of the invention the radioactive atom is selected from the group consisting of technetium-99m, iodine-123, iodine-125, iodine-131, indium-111, fluorine-19, carbon-13, nitrogen-15, oxygen-17, phosphorus-32, sulphur-35, deuterium, tritium, rhenium-186, rhenium-188 and yttrium-90.

A third aspect of the invention provides a method of diagnosing or prognosing a lymphoma in an individual, the method comprising:
(a) providing a sample of cells from the individual; and
(b) determining the amount of Sox11 protein and/or mRNA in the sample of cells.
wherein the levels of Sox11 protein and/or mRNA are indicative of the individual having mantle cell lymphoma.

In one embodiment, the lymphoma is a mantle cell lymphoma (MCL). For example, the method may be for diagnosing MCL.

In a further embodiment, the lymphoma is a diffuse large B-cell lymphoma (DLBCL). For example, the method may be for prognosing DLBCL.

It will be appreciated by skilled persons that the methods of the third aspect of the invention may be performed in vivo or in vitro.

In one embodiment, the method comprises the detection of Sox11 expression as a sole biomarker for lymphoma (as discussed above).

Alternatively, the binding moiety of the invention may be used in combination with one or more additional binding moieties for detecting one or more additional biomarkers for lymphoma. Thus, the binding moiety may be used in combination with fewer than 20 additional binding moieties, for example fewer than 15, 10, 8, 6, 5, 4, 3, 2 or 1 additional binding moieties.

Preferably the sample of cells to be tested is in the form of a tissue sample. More preferably the sample of cells to be tested comprises or consists of lymph node cells. Even more preferably the amount of Sox11 protein and/or mRNA in the sample is performed using a binding moiety as described above.

A further embodiment of the third aspect of the invention comprises comparing the amount of Sox11 protein and/or mRNA in the sample of cells to be tested with the amount of Sox11 protein and/or mRNA in a control sample.

Advantageously the control sample is a negative control sample comprising or consisting of non-cancerous B cells. More advantageously the control sample is a positive control sample comprising or consisting of cancerous cells. Conveniently the cancerous cells are B cells.

Preferably the control sample comprises cells selected from the group consisting of mantle cell lymphoma cells, precursor B-lymphoblastic leukaemia/lymphoma cells, chronic lymphocytic leukaemia/lymphoma (CLL) cells, plasma cell myeloma cells, extra nodal marginal zone B cells lymphoma of mucosa-associated lymphoid tissue type cells, follicular lymphoma (FL) cells, diffuse large B cell lymphoma (DLBCL) cells, hairy cell leukaemia (HCL) cells and Burkitt lymphoma cells.

Typically, step (b) of the third aspect of the invention is performed using a method selected from the group consisting of macroarray screening, microarray screening, nanoarray screening, reverse transcription PCR, real-time PCR or in situ PCR.

A further embodiment of the third aspect of the invention comprises determining the levels of CD23 and/or CD10 and/or BCL1 and/or CD5 protein and/or mRNA in the sample to cells to be tested.

A fourth aspect of the invention provides a method of imaging lymphoma cells in the body of an individual, the method comprising administering to the individual an effective amount of a binding moiety as described above.

In one embodiment, the lymphoma is a mantle cell lymphoma (MCL).

In a further embodiment, the lymphoma is a diffuse large B-cell lymphoma (DLBCL).

The term 'effective amount' as used herein, refers to that amount which provides a sufficiently detectable signal for a given administration regimen. This is a predetermined quantity of active material calculated to produce a desired signal strength in association with the required additive and diluent, i.e. a carrier or administration vehicle. As is appreciated by those skilled in the art, the amount of a compound may vary depending on its specific activity. Suitable dosage amounts may contain a predetermined quantity of active composition calculated to produce the desired signal strength in association with the required diluent. In the methods and use for manufacture of compositions of the invention, an effective amount of the active component is provided. An effective amount can be determined by the ordinary skilled medical or veterinary worker based on patient characteristics, such as age, weight, sex, condition, complications, other diseases, etc., as is well known in the art.

Typically the fourth aspect of the invention comprises the step of detecting the location of the binding moiety in the individual. Preferably Sox11 protein and/or mRNA encoding the same is used as a marker for mantle cell lymphoma cells.

A fifth aspect of the invention provides the use of a binding moiety as defined above in the preparation of a medicament for diagnosing or prognosing mantle cell lymphoma.

The invention additionally provides the use of Sox11 protein and/or mRNA encoding the same as a biomarker for lymphoma cells.

In one embodiment, the lymphoma is a mantle cell lymphoma (MCL).

In a further embodiment, the lymphoma is a diffuse large B-cell lymphoma (DLBCL).

It will be appreciated that Sox11 may be used as a sole biomarker for lymphoma.

Alternatively, Sox11 may be used in combination with one or more additional biomarker. Preferably, however, Sox11 is used in combination with fewer than 20 additional biomarkers are used in the method, for example fewer than 15, 10, 8, 6, 5, 4, 3, 2 or 1 additional biomarkers.

A further aspect of the invention provides a method of screening for a molecule with efficacy in the diagnosis and/or prognosis of a lymphoma, the method comprising the steps of:
(a) contacting a molecule to be tested with Sox11 protein and/or mRNA encoding the same (or with a fragment of said protein or mRNA); and
(b) detecting the presence of a complex containing the protein and/or mRNA (or fragment thereof) and the molecule to be tested.

In one embodiment, the lymphoma is a mantle cell lymphoma (MCL).

In a further embodiment, the lymphoma is a diffuse large B-cell lymphoma (DLBCL).

Methods of detecting and/or measuring the concentration of protein and/or nucleic acid are well known to those skilled in the art, see for example Sambrook and Russell (supra.).

Preferred methods for detection and/or measurement of protein include Western blot, North-Western blot, immunosorbent assays (ELISA), antibody microarray, tissue microarray (TMA), immunoprecipitation, in situ hybridisation and other immunohistochemistry techniques, radioimmunoassay (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference. Antibody staining of cells on slides may be used in methods well known in cytology laboratory diagnostic tests, as well known to those skilled in the art.

Typically, ELISA involves the use of enzymes which give a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemi-luminescent systems based on enzymes such as luciferase can also be used.

Conjugation with the vitamin biotin is frequently used since this can readily be detected by its reaction with enzyme-linked avidin or streptavidin to which it binds with great specificity and affinity.

Preferred methods for detection and/or measurement of nucleic acid (e.g. mRNA) include southern blot, northern blot, polymerase chain reaction (PCR), reverse transcriptase PCR (RT-PCR), quantitative real-time PCR (qRT-PCR), nanoarray, macroarray nanoarray, autoradiography and in situ hybridisation.

In a typical embodiment the presence of lymphoma cells is detected by detection of Sox11 protein and/or nucleic acid in cell nuclei. Preferably, the nuclei of lymphoma cells express Sox11 protein and/or nucleic acid in a relatively high amount, as indicated, for example, by bright staining of the nuclei during in situ hybridisation analysis. Characteristically, absent or relatively low Sox11 protein and/or nucleic acid expression of cell nuclei is indicative of non-lymphoma cells.

Preferred, non-limiting examples which embody certain aspects of the invention will now be described, with reference to the following figures:

FIG. 1. A TMA montage of representative Sox11 IHC signals in each category tested includes rows of benign tonsillar germinal centers (GC), follicular lymphoma (FL, with tumor grade at the bottom right), chronic lymphatic leukemia/small cell lymphoma (CLL) and mantle cell lymphoma (including blastoid variant in the third image from the left). Each section in the first three rows displays granular cytoplasmic staining. A single positive nucleus in the second FL section is probably endothelial. In contrast, most MCL nuclei express Sox11 with varying intensity. Hematoxylin counterstain, 185x FIG. 2. Sox11 immunohistochemical analysis of cyclin D1 negative cases of MCL showing staining of a single case with high frequency (22%) of nuclei positive for the t(11; 14) translocation as determined with FISH analysis, while the remaining cases are negative.

Figure 3:
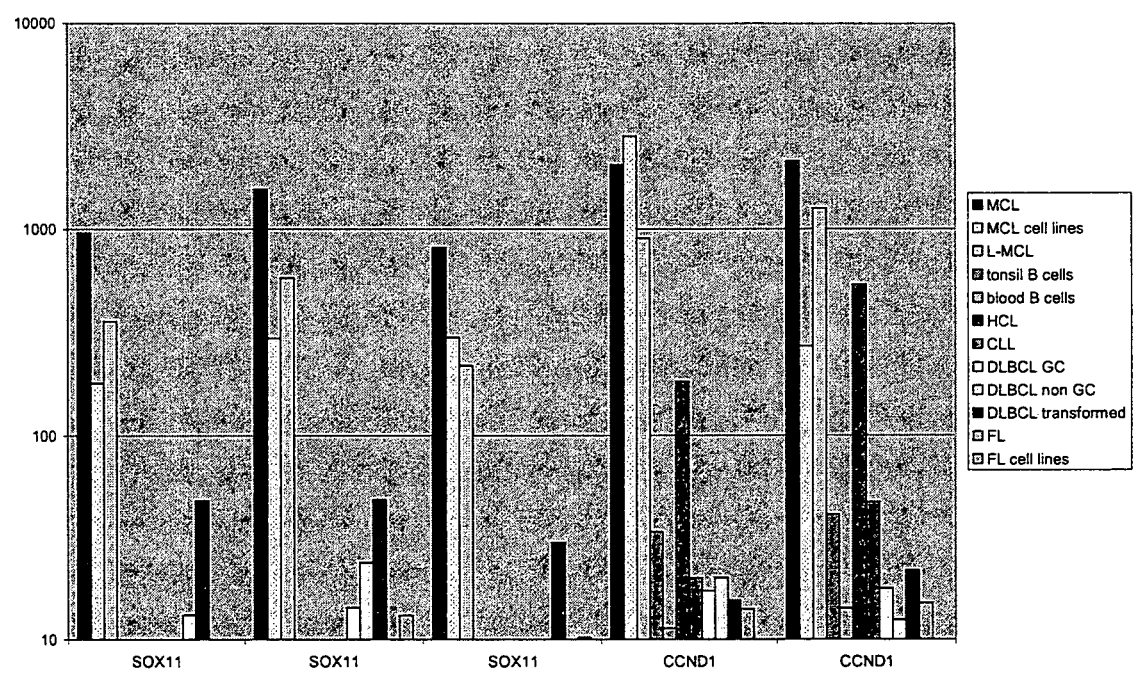

FIG. 3. The average transcriptional level (scaled raw values) of SOX11 and cyclin D1 for different B cell lymphomas primary samples, MCL and FL cell lines and benign tonsil and blood B cell reference material is illustrated. The genes are represented by two (cyclin D1) or three (SOX11) different probes on the array as described in material and methods. The expression level of SOX11 is on average 10-100 times higher for MCL, L-MCL and MCL cell lines than the other cases, as is the expression of cyclin D1 with the exception of HCL, which also express cyclin D1.

FIG. 4. Amino acid sequence of *Homo sapiens* Sox11 protein.

FIG. 5. Nucleic acid sequence of *Homo sapiens* SOX11 mRNA.

Figure 6:
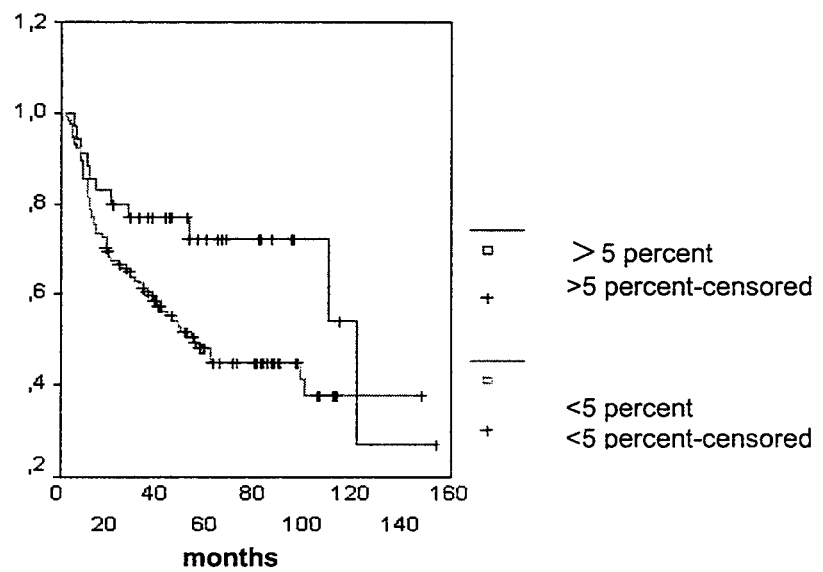

FIG. 6. Survival time for DLBCL patients with high levels or low levels of SOX11.

Figure 7:
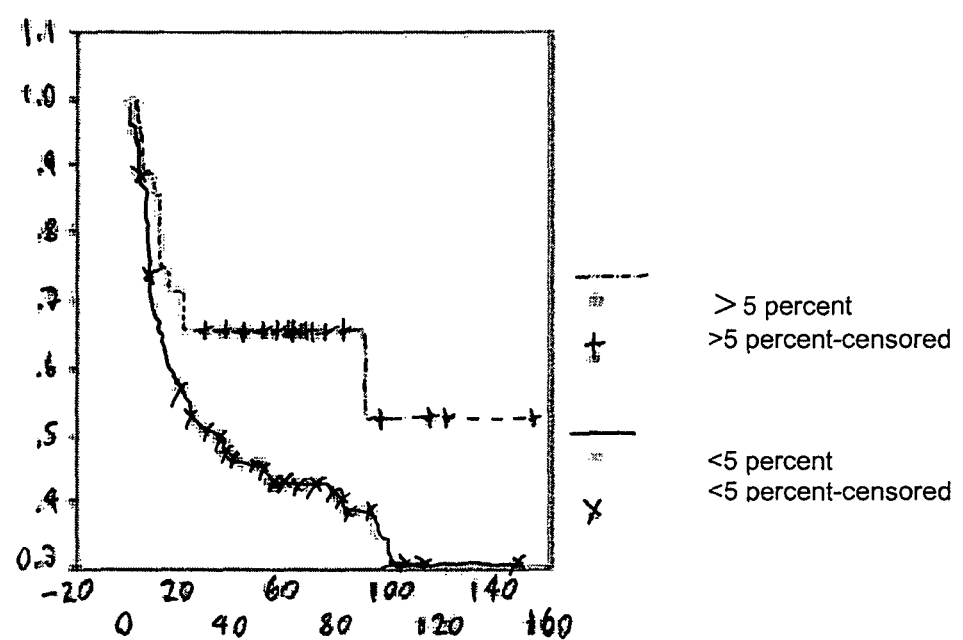

FIG. 7. Time to relapse for DLBCL patients with high levels or low levels of Sox11.

EXAMPLES

Example A

Mantle Cell Lymphoma

Materials and Methods

Immunohistochemistry Analysis
Sox-11.
The expression of Sox11 was investigated by Immunohistochemical (IHC) analysis of different types B cell lymphomas and non-malignant control tissues (see Table 1-4). Briefly 2-4 µm paraffin tissue sections from different lymphoma or leukemia subtypes as well as benign B cells (Department of Pathology, Lund University Hospital archives or Division of Pathology, Malmö University Hospital) were deparaffinized and rehydrated. An electric decloaking chamber was utilized for antigen retrieval, sections were immersed in BORGdecloaker (Biocare, Concord, Calif., USA) at pH 9.0 and then stained with a primary antibody rabbit anti-human Sox11 (1/100) at room temperature for 25 minutes. The antibody targets the following protein sequence:

[SEQ ID NO: 3]
FMVWSKIERRKIMEQSPDMHNAEISKRLGKRWKMLKDSEKIPFIREA

ERLRLKHMADYPDYKYRPRKKPKMDPSAKPSASQSPEKSAAGGGG

GSAGGGAGGAKTSKGSSKK and was raised by the HPR-project as previously described (Ek et al., 2006, *Mol Cell Proteomics.*, 5:1072-1081; Agaton et al., 2003, *Mol Cell Proteomics.*, 2:405-414). Signals were detected using Dako REAL Detection system, containing the secondary biotinylated goat anti rabbit/mouse antibody, the substrate streptavidin/horseradish peroxidase complex and 3,3'-diaminobenzidine, according to manufacturer's protocol. The slides were counterstained with Mayers hematoxylin (Sigma-Aldrich).

Cyclin D1.

For IHC determination of cyclin D1 (CCND1) sections were microwaved in EDTA buffer for antigen retrieval and immunostained as above using a highly sensitive rabbit monoclonal anti-CCND1 antibody (NeoMarkers, USA) at a dilution of 1:100 (Cheuk et al., 2004, *Am J Surg Pathol.*, 28:801-807) for whole sections and mouse monoclonal anti-CCND1 antibody diluted 1:50 (Clone DSC-6, DAKO A/S, Denmark) for tissue microarray sections.

Tissue Microarray

SOX11 expression was also analyzed in a TMA containing a mixture of B-cell derived lymphomas diagnosed in the Department of Pathology, Malmö University Hospital. After histopathological re-evaluation including immunohistochemical profiling with a standard diagnostic panel of antibodies (Bcl-2, Bcl-6, CD3, CD5, CD10, CD23, CD30, CD79, Cyclin D1), 10 cases of MCL, 27 cases of CLL, 27 cases of FL and 30 cases of DLBCL were selected for TMA construction. Tonsils from 3 healthy individuals were used as reference tissue. Representative, non-necrotic, tumour areas were marked on H&E stained sections and two 1.00 mm tissue cores were then removed from each corresponding paraffin block and assembled in a new recipient block using an automated device (ATA-27, Beecher Inc., Wisconsin, USA).

PCR Analysis

All biologic material was de-identified and used according to the research ethics principles established for our institution. In four cryopreserved CCND1⁻ MCL samples DNA template was used in a PCR with a primer set reported to detect ~40% of BCL1/IGH fusions resulting from t(11; 14) (q13; q32), characteristic of MCL (van Dongen et al., 2003, *Leukemia*, 17:2257-2317).

qRT-PCR Analysis of Cyclin D1

Tissue from the above four samples was disrupted and RNA was extracted in a guanidinium isothiocyanate buffer, isolated on a silicon gel membrane (Qiagen RNeasy®) and treated with DNase I. cDNA synthesis utilized random hexamers (Invitrogen), 1× buffer RT, 0.5 mM/dNTP mix and 4 units of reverse transcriptase (all Omniscript®, Qiagen) plus 20 units of RNase inhibitor (Invitrogen). We used a fluorogenic 5' nuclease assay to determine $C_T$ values on a Rotorgene cycler running software vers. 6 (Corbett Research). TBP, which codes a TATA box binding protein in the TFIID complex involving RNA polymerase II, has been previously validated as a reference gene in lymphocytes and its expression is relatively stable; the TBP product (73 bp) spanned two introns of 2.3 kbp and the CCND1 product (70 bp) spanned a single intron (1.4 kbp). Each primer set was run in separate reactions and each sample was run in triplicate. Each run also had the cell line Granta 519 cDNA as a positive control, one negative water control and two no template controls using DNase I-treated RNA which had not been reverse transcribed.

The CCND1 reaction mix contained in a final volume of 25 µL: TaqMan® Universal PCR Master Mix, No AmpErase® UNG, 12.5 µL (Applied Biosystems), 0.9 µM forward CCND1 primer, 0.3 µM of reverse primer, 0.2 µM probe and 2 µL cDNA. For TBP both primers were at 0.3 µM. Cycling conditions were 95° C. for 10 min, followed by 50 cycles at 95° C./15 sec and annealing at 60° C./1 min.

Gene expressions were calculated to determine the fold increase in normalized CCND1 $C_r$ values relative to a so-called calibrator, in this case a benign node, using the formulas (Livak and Schmittgen, 2001, *Methods*, 25:402-408):

$\Delta C_T = (C_{T,CCND1} - C_{T,TBP})$ where $\Delta C_T$ is the difference between the threshold cycle numbers of the target and reference genes at which the concentration of target amplicons reaches a fixed level; and $-\Delta\Delta C_T = -(\Delta C_{T,q} - \Delta C_{T,cb})$ where $-\Delta\Delta C_T$ is the difference in the above equation for any sample q compared to the calibrator, cb. The validity of this method was confirmed in a larger set of MCL in which mRNA fold changes corresponded to CCND1 expression (data not shown, manuscript submitted).

FISH

Fluorescence In Situ Hybridization (FISH) analysis was used to identify cases with t(11; 14) translocation. In order to avoid artefacts associated with sectioning (Ventura et al., 2006, *J Mol Diagn.*, 8:141-151) we isolated whole nuclei from 40-µm-thick paraffin sections deparaffinized in xylene and then hydrated. Samples were digested in 4 mg/mL pepsin (Sigma P7012, 0.9%. NaCl, pH 1.5), passed through a 41 µm nylon net filter, pelleted, suspended in PBS, washed and spread on a ThinPrep slide (Cytyc, USA), which was dried 1 h, fixed in Carnoy's fixative (3:1 metanol:acetic acid) 10 min and air-dried for 1 h.

Prehybridization.

Slides were placed in PBS with 0.1% Triton-100 for 2 min, rinsed, digested in 0.3 mg/mL pronase (Roche, Germany) in 50 mM Tris/HCl, 5 mM EDTA, pH 7.6 for 5 min, dehydrated in ethanol and air-dried.

Hybridization.

The LSI® IGH/CCND1 XT dual color, dual fusion translocation probe (Vysis, Downers Grove, USA) labeled with SpectrumOrange (CCND1) and SpectrumGreen (IGH) was prepared and hybridized according to the manufacturer's instructions. This probe hybridizes to both target genes and their flanking sequences, allowing visualization of derivative chromosomes in t(11; 14)(q13; q32) as separate yellow fusion signals.

Posthybridization.

The coverslip was removed and the slide rinsed in SSC (299 mM NaCl, 30 mM sodium citrat, pH 7.0 with 50% formamide) in a 45° C. water bath for 1 min. Then the slide was treated with 2×SSC, 1 min @ RT rinsed in 2×SSC/0.1% NP-40, 2×1 min at RT. After air-drying for 10 min the slide was coated with 10 µl of DAPI II (125 ng/mL of 4,6-diamidino-2-phenylindole in 1,4-phenylenediamine, Vysis Inc.), coversliped and viewed in an Olympus BX-40 epifluorescence microscope equipped with a 100 W lamp and a red-green dual bandpass (588 nm/538 nm) filter.

Scoring.

For each specimen 50 nuclei were scored for number of fusion signals using a cut-off value of 2% based on fusion counts in 350 total nuclei non-MCL nodes.

mRNA Analysis of Sox11 and Cyclin D1

All B cell lymphomas and reference samples were purified using flow cytometry assisted cell sorting and the isolated RNA were run on Affymetrix U133 Plus 2.0 as previously described (see Andréasson et al., 2008, *Cancer Lett.* 259(2): 138-45). The probe sets available for the SOX11 genes is 204913_s_at, 204914_s_at and 204915_s_at. Cyclin D1 is represented by 208711_s_at and 208712_at. The value for the individual probe sets are displayed in FIG. 3 in the above mentioned order.

Results

In this study, Sox11 has been investigated as a potential antigen for differential diagnosis of B cell lymphomas. Paraffin-embedded diagnostic archive material was used to assess the expression of Sox11 in various entities of B cells lymphomas and reference material. Interestingly, both whole MCL tissue sections (17/18, Table 1 and 2) and TMA of MCL (9/10, Table 3) showed nuclear staining of Sox11, while other lymphomas generally were negative or showed cytoplasmic staining. An overview of the results from the immunohistochemistry analyses is shown in FIG. 1.

Immunohistochemical Analysis

Sox-11 IHC Staining of Whole Tissue Section of B Cell Lymphomas and Tonsil Reference Material.

Staining for Sox11 on whole MCL tissue sections resulted in nuclear staining of the majority of cases (17/18, Table 1 and 2). For most of these positive cases the nuclear staining was bright and found in the majority of the tumor cells (14/17), while three cases showed fewer positive nuclei but had a distinct cytoplasmic staining of the majority of the tumor cells (FIG. 1). Analysis of whole tissue sections of follicular lymphoma (FL), chronic lymphocytic leukemia/lymphoma (CLL) and reference material showed that for FL, 15/20 cases were negative and the remaining five cases showed cytoplasmic staining of Sox11, CLL were negative in 18/20 cases and showed cytoplasmic staining in the remaining two and finally tonsil reference material showed no or cytoplasmic staining in 2/4 cases, respectively. The cytoplasmic staining of the various lymphomas was easily distinguished from the bright nuclear staining of the majority of MCLs.

Sox11 IHC Staining of Tissue Microarrays of B Cell Lymphomas and Tonsil Reference Material.

Tissue microarrays of MCL, CLL, FL, DLBCL (diffuse large B cell lymphoma) and reference tonsil material were also analyzed (Table 3 and FIG. 1). MCL showed positive nuclear staining of Sox11 in 9/10 cases and cytoplasmic staining in 1/10 cases. Sections of CLL showed no staining in the majority of cases (19/27) and cytoplasmic Sox11 staining in eight cases. FL showed similar results where 22/27 cases showed no staining and the remaining five cases showed cytoplasmic staining. Like CLL and FL, DLBCL were negative in the majority of cases (17/30) and showed cytoplasmic staining of Sox11 in ten cases. Moreover, a few cases of DLBCL (3/30) showed weak and diffuse nuclear staining, clearly distinct from the bright nuclear staining of MCLs. Tonsil tissue sections were used as reference material and 2/3 cases on the TMA showed no staining while a single case showed cytoplasmic staining of Sox11 in the cells populating the B cell follicle. In all cases of reference tonsil material strong nuclear staining of epithelial cells were seen.

Sox11 IHC Staining of Cyclin D1-Negative MCL Cases.

Figure 2:
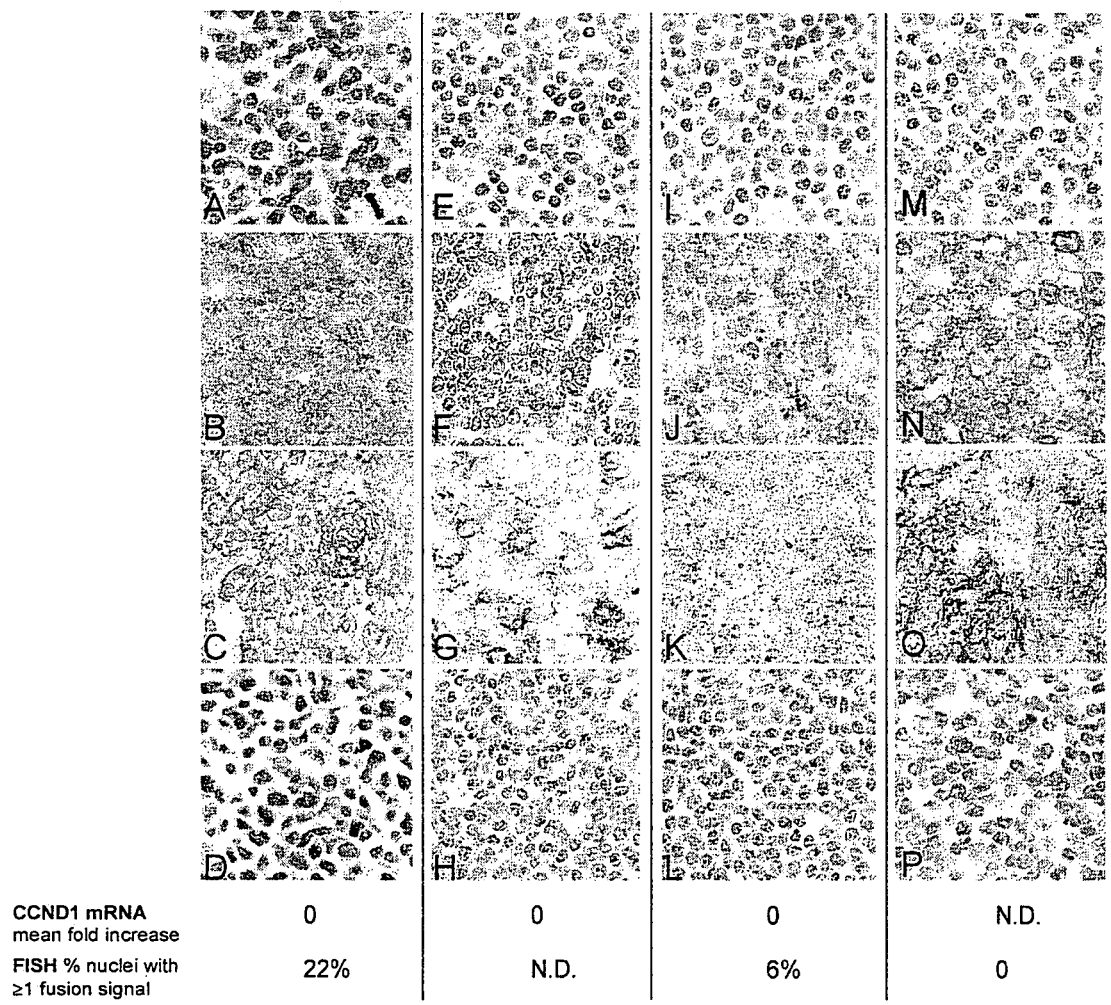

Staining of Sox11 was analyzed in four cases of cyclin D1 negative MCLs (FIG. 2). These cases had been diagnosed based on morphological features (three cases) as there was no detection of either cyclin D1 transcript, cyclin D1 protein or BCL1/IG transcript. In addition, three out of the four cases showed no or very low frequency of cyclin D1 translocation (t(11; 14)) as assessed by FISH analysis, while a single case showed sign of t(11; 14) in 22% of the analyzed nucleus.

Sox11 were negative or showed weak cytoplasmic staining for most of the cases but a bright nuclear staining was seen for the cyclin D1 negative MCL case with high frequency of t(11; 14).

Sox11 IHC Staining of Various Reference Materials.

To more widely investigate the expression of Sox11 in different human tissues a TMA focused on non-malignant material was used (Table 4). Nuclear staining of Sox11 was only seen in keratinocytes and squamous cells, while all other tissue including, bone marrow and brain had cells with negative nucleus. However, several cell types and tissues showed cytoplasmic staining for Sox11, including enterocytes, hepatocytes as well as cells in the pancreas and prostate.

mRNA Levels of SOX11 and CCND1/BCL1 in Various B Cell Lymphomas and Reference Samples.

The SOX11 and CCND1/BCL1 mRNA level was assessed using a material of different B cell lymphomas and reference samples run on Affymetrix U133 Plus 2.0 arrays (FIG. 3). The SOX11 transcriptional level is 10-100 times higher for the MCL samples compared to most other B cell lymphomas (FIG. 3). Not only primary MCL showed high expression of SOX11 but elevated levels were also seen in samples of leukemic MCL (L-MCL) and MCL cell lines. A few samples of DLBCL also show elevated levels of SOX11 mRNA, as represented by an increased average value, correlating well with the variation seen on protein level using IHC analysis.

CCND1/BCL1 transcript levels were as expected high in all types of MCL samples, including nodular and leukemic MCL, and also in samples of hairy cell leukemia (HCL).

TABLE 1

IHC Staining of Sox11 and cyclin D1 on whole MCL tissue sections

| Entity | Case ID | Sox11 | Description | cyclin D1 | t(11; 14)* |
|---|---|---|---|---|---|
| MCL | 1 | Positive | Nuclear staining | Positive | Positive |
| MCL-BV | 2 | Positive | Strong nuclear staining | Positive | Positive |
| MCL | 3 | Positive | Nuclear staining and localized cytoplasmic staining | Positive | N.D. |
| MCL | 4 | Few cells nuclear Positive | Cytoplasmic staining and weak nuclear staining in a fraction of the tumor cells. | Positive | N.D. |
| MCL | 5 | Positive | Nuclear staining | Positive | Positive |
| MCL-BV | 6 | Negative | Negative, some background | Positive | Positive |
| MCL | 7 | Positive | Strong nuclear staining | Positive | N.D. |
| MCL | 8 | few cells positive | Cytoplasmic staining and granular nuclear staining in a fraction of the tumor cells | Positive | N.D. |
| MCL-PT | 9 | Positive | Strong nuclear staining | Positive | N.D. |
| MCL | 10 | Positive | Nuclear and localized cytoplasmic staining | Positive | N.D. |
| MCL | 11 | Positive | Strong nuclear staining | Positive | N.D. |
| MCL | 12 | Positive | Nuclear staining | Positive | N.D. |
| MCL | 13 | Positive | Strong nuclear staining | Positive | N.D. |

TABLE 1-continued

IHC Staining of Sox11 and cyclin D1 on whole MCL tissue sections

| Entity | Case ID | Sox11 | Description | cyclin D1 | t(11; 14)* |
|---|---|---|---|---|---|
| MCL | 14 | Positive | Nuclear staining | Positive | N.D. |
| MCL | 15 | Positive | Nuclear staining | Positive | N.D. |
| MCL | 16 | Positive | Strong nuclear staining | Positive | N.D. |
| MCL | 17 | Positive | Nuclear staining | Positive | N.D. |
| MCL | 18 | Few cells nuclear positive | Cytoplasmic staining and granular nuclear staining in a fraction of the tumor cells | Positive | N.D. |

MCL-BV, MCL with blastoid variant;
MCL-PT, MCL with pleomorph type,
ND, not determined
*The t(11; 14) translocation was assessed using FISH

TABLE 2

Summary of Sox11 IHC stainings on whole tissue sections of B cell lymphomas and tonsil reference material.

| Entity | Number of cases | No staining | Cytoplasmic staining and weak nuclear staining | Nuclear staining |
|---|---|---|---|---|
| MCL | 18 | 1 | 3 | 17 |
| CLL | 20 | 18 | 2 | 0 |
| FL | 20 | 15 | 5 | 0 |
| Tonsil-GC | 4 | 2 | 2 | 0 |

TABLE 3

Summary of Sox11 IHC stainings on TMA sections of B cell lymphomas and tonsil reference material.

| Entity | Number of cases* | No staining | Cytoplasmic staining | Nuclear staining |
|---|---|---|---|---|
| MCL** | 10 |  | 1 | 9 (strong) |
| CLL | 27 | 19 | 8 | 0 |
| FL | 27 | 22 | 5 | 0 |
| DLBCL | 30 | 17 | 11 | 2 (weak to moderate) |
| tonsil | 3 | 2 | 1 | 0 |

*all cases were run in duplicates
**one case of MCL was originally diagnosed as DLBCL but changed to MCL based on immunohistochemical stainings showing both cyclin D1/CD5 positivity and CD10/bcl-6 negativity.

TABLE 4

Summary of Sox11 IHC stainings on TMA sections of various tissues.

| | | IHC staining | |
|---|---|---|---|
| Cell type | Organ | Nuclear | Cytoplasmic |
| Schwann | Peripheral nerve | Positive | Negative |
| Keratinocyte | Skin | Positive | Positive |
| Squamous Epithelium | Tonsil | Positive | Negative |
| | Bronchus | Scattered Positive | Positive |
| Follicular epithelium | Thyroidea | Occ. weak positive | Positive |
| Enterocyte | Appendix | Negative | Positive |
| | Colon | Negative | Positive |
| Hematopoietic | Bone marrow | Negative | Negative |
| Cerebral cortex | Adult brain | Negative | Negative |
| Acinar epithelium | Breast | Negative | Negative |
| | Pancreas | Negative | Positive |
| | Prostate | Negative | Positive |
| Hepatocyte | Liver | Negative | Positive |
| Renal tubule | Kidney | Negative | Positive |
| Glomeruli | | Negative | Negative |
| Melanoma | Skin | Negative | Positive |
| Skeletal muscle | | Negative | Negative |
| Trophoblast | Placenta | Negative | Negative |
| Smooth muscle | Uterus | Negative | Positive |

Discussion

We herein present the novel finding that the non B-cell lineage transcription factor Sox11 is specifically expressed in MCL compared to other B cell lymphomas and non-malignant tissue (Table 1-4 and FIG. 1-3).

Sox11 is normally expressed throughout the central nervous system in human embryo and thus seems to have a role in the developing nervous system (Cheung et al., 2000, *Brain Res Mol Brain Res.*, 79:180-191). Q-RT-PCR analysis has not only confirmed expression in fetal brain but also showed Sox11 overexpression in malignant gliomas compared to normal adult brain and other organs (Weigle et al., 2005, *Oncol Rep.*, 13:139-144).

In contrast, it has been shown that many adult tissues, for example, spleen, thymus, prostate, testis, ovary, small intestine, colon, peripheral blood, leukocyte, heart, brain, placenta, lung, liver, skeletal muscle, kidney and pancreas, are negative for Sox11 mRNA (Jay et al., 1995, *Genomics.*, 29:541-545). The lack of expression in adult brain and leukocytes correlates with our results but in opposite to the study performed on mRNA, we detected cytoplasmic staining of the Sox11 protein in kidney, liver, lung and pancreas (Table 4).

The function of Sox11, and many of the other members of the Sox HMG box super family is not clear (Wegner M et al., 1999, *Nucleic Acids Res.*, 27:1409-1420). Sox HMG domains have been found to bind to the consensus sequence 5"-(A/T)(A/T)CAA(A/T)G-3' in the minor groove of DNA (Harley V R, 1994, *Nucleic Acids Res.*, 22:1500-1501) and induce a large conformational change in the DNA (Werner et al., 1995, *Cell*, 81:705-714). It has been suggested that the function of the Sox proteins are at least partly architectural, allowing other transcription factors to bind the major groove, and/or bringing together regulatory element and thereby facilitating the formation of protein complexes (Dong et al., 2004, *Cytogenet Genome Res.* 105:442-447).

Furthermore Sox11 has, similarly to other transcription factors, found to have an acidic auto inhibitory region that repress the DNA binding capacity and reduce gene activation in vivo (Wiebe et al., 2003, *J Biol Chem.* 278:17901-17911). DNA binding is likely permitted by neutralizing the auto-inhibitory domain through post-translation modification and/or direct interactions with partner proteins through specific binding (Wiebe et al., 2003, *J Biol Chem.* 278:17901-17911).

There is growing support for a model in which the HMG domain serves two functions, (i) DNA binding and (ii) partner selection, which may permit selective recruitment of individual sox proteins to specific genes. Amongst others, the function of Sox 11 and Sox2 and their interaction with two Pit-Oct-Unc (POU) proteins, Oct-3 and Brn-2 has been studied in the human system. It was shown that both proteins cooperated with Oct-3, while only Sox11 could partner with Brn-2 to activate transcription (Wiebe et al., 2003, *J Biol Chem.* 278:17901-17911). It has previously been shown that Brn-2 is involved in proliferation in melanoma tumor cells and can, like cyclin D1, be induced by the WNT/Beta-catenin pathway (Larue and Delmas, 2006, *Front Biosci.*, 11:733-742).

Interestingly, it has been shown that one of the other sox family members, Sox6 suppresses cyclin D1 promoter activity by interacting with Beta-catenin (Iguchi et al., 2007, *J Biol Chem.*) exemplifying the complex regulation of genes. Consequently, the expression and use of individual sox proteins may specifically promote the activity of certain transcriptions factors, like the POU proteins, and thus influence vital cell functions. It has already been shown that Oct-2, which is a POU transcription factor, acts as a cell survival factor in lymphoma cells harbouring the t(14; 18) translocation, by directly activating the anti-apoptotic gene bcl-2 (Heckman et al., 2006, *Oncogene.*, 25:888-898). Although this has not been associated with Sox activation, it indicates the effect that Sox-induced activation of POU protein might have.

More functional studies have been performed in the murine system and it has been shown using primary and continuous cell cultures that neuron survival and neurite growth is dependent on Sox11 (Jankowski et al., 2006, *Neuroscience*, 143: 501-514). Its role in tissue remodeling has also been studied in a knock-out mouse model showing various malformations, indicating that Sox11 is important for tissue remodeling and that mutated Sox11 in humans potentially can correspond to malformation syndromes (Sock et al., 2004, *Mol Cell Biol.*, 24:6635-6644). Furthermore, using siRNA knock-down in a neuroblastoma cell line and in cultured mouse dorsal root ganglia neurons it was shown that knock-down of Sox11 modulated the level of mRNAs encoding several genes related to cell survival and death, for example, increased expression of the pro-apoptotic gene BNIP3 and decreased expression of the anti-apoptotic gene TANK (TNF receptor-associated factor family member-associated NFκB activator) (Jankowski et al., 2006, *Neuroscience*, 143:501-514).

Thus, although the function in the human system is not clear it can be hypothesized that the overexpression of Sox11 in MCL may lead to aberrant regulation of genes involved in cell survival and/or death. This is further supported by the fact that many of the Sox genes have been shown to be involved in different types of cancer as reviewed by Dong et al. (Dong et al., 2004, *Cytogenet Genome Res.* 105:442-447) Sox4, which is highly homologous to Sox11, has been identified as a potential regulator of the human breast cancer oncogene, HER2/neu (c-ErbB2) (Chang et al., 1997, *Oncogene*, 14:1617-1622) and both Sox4 and Sox11 are strongly expressed in most medulloblastomas, anaplastic oligodendrogliomas and glioblastomas.

In this study, we show that Sox11 also is specifically overexpressed in MCL compared, not only to benign tissue, but also to other B cell lymphomas both at the mRNA level (FIG. 3) and at the protein level (FIG. 1 and Table 1-3). mRNA analysis of the different malignancies show, as expected, high overexpression of cyclin D1 in MCL and HCL, but more surprisingly also >100× overexpression of Sox11 in MCL compared to the other tissues (FIG. 3). The overexpression of Sox11 was in many cases not only quantitative but also qualitative as most non-MCL cases showed no expression of the transcript. Furthermore, the use of Sox11 was not restricted to primary nodular MCL but also L-MCL and MCL cell lines expressed the transcript at high levels (FIG. 3).

At the protein level, cyclin D1 positive MCL showed nuclear staining of Sox11 in 93% (26/28) of the cases and was in the majority of cases bright, while a few cases (3/28) showed both weaker and less frequent nuclear staining as shown in FIG. 1. No cases of bright nuclear staining were seen for DLBCL, FL, CLL or reference tonsil material, although some of the cases showed cytoplasmic staining as shown in FIG. 1.

The cytoplasmic localization of Sox11 detected in some of the cases can not be explained. The nuclear localization signals are conserved among all Sox proteins (Poulat et al., 1995, *J Cell Biol.*, 128:737-748; Sudbeck and Scherer, 1997, *J Biol Chem.*, 272:27848-27852) and although a nuclear export signal has been found within the group E sox proteins (Sox8-10), (Gasca et al., 2002, *Proc Natl Acad Sci USA*, 99:11199-11204; Rehberg et al., 2002, *Mol Cell Biol.*, 22:5826-5834) this has not yet been shown for Sox11. Interestingly, proteins with both nuclear import and export sequences will continuously shuttle between the cytoplasm and the nucleus (Wegner, 2005, *Cell Res.*, 18:74-85) and for Sox10 this has been shown to be essential for the function of the protein (Rehberg et al., 2002, *Mol Cell Biol.*, 22:5826-5834).

To also test the diagnostic potential of Sox11 for MCLs lacking the characteristic cyclin D1 protein expression, four cases of cyclin D1 negative MCL cases were analyzed. Sox11 only showed staining of the case with a high number of nucleus positive for the translocation. This suggests that Sox11 may be useful in routine IHC to identify both cyclin D1 positive and negative MCLs.

The current criteria for diagnosis of MCL rely on the World Health Organization guidelines stating that MCL diagnosis is based on morphologic examination and immunophenotyping, with demonstration of cyclin D1 protein overexpression and/or the t(11; 14)(q13; q32) (Harris et al., 2000, *Mod Pathol.*, 13:193-207). This definition relies on the fact that cyclin D1 negative MCL, which were diagnosed based on morphological and phenotypical examination, have a significant better survival than the cyclin D1 positive MCL, thus defining a separate entity (Yatabe et al., 2000, *Blood.*, 95:2253-2261). However, lately others have shown that there are cases which lack both the t(11; 14) translocation and the cyclin D1 protein but that still have a similar gene expression profiling to classical cyclin D1 positive MCL and that these should be considered to belong to the MCL entity (Fu K et al., 2005, *Blood.* 106:4315-4321).

Our results support the current definition that a valid diagnosis of MCL should include either the cyclin D1 protein or the t(11; 14) translocation. From our results it is also clear that there is no general co-regulation of cyclin D1 and Sox11 mRNA, as HCL that express cyclin D1, lack expression of Sox11. However, HCL express cyclin D1 independent of chromosomal rearrangements (de Boer et al. 1996, *Ann*

Oncol. 7:251-256), which might suggest that the overexpression of Sox11 in MCL is correlated to the t(11; 14) translocation.

In summary, in this study we present the novel finding that Sox11 is specifically expressed in the nucleus of MCL, while other B cell lymphomas show no staining or cytoplasmic staining. Thus, Sox11 not only shows great potential for diagnostic use, as a strong complement to cyclin D1, for specific diagnosis of cyclin D1 negative and positive MCL but also indicates an important functional role for this antigen in the survival and/or transformation of MCL tumor cells.

Example B

Diffuse Large B-Cell Lymphoma

This study demonstrates that cytoplasmic staining of Sox-11 correlates to survival and time to relapse in diffuse Large B cell lymphoma.

In the present study, 153 patients were selected for analysis of the correlation of Sox-11 expression with overall survival and time to relapse. All staining with anti-Sox-11 were performed on triplicate cores from each patient, mounted as tissue microarrays. The staining was both evaluated manually but also using an automated evaluation of the area of the section that stained positive for Sox-11. All staining were cytoplasmic staining, while almost no nuclear staining was seen for DLBCL (151/153 negative for nuclear staining), which is quite the opposite to MCL, as previously described by us (Ek et al., 2008, Blood 111, 800-805). The cut-off for positive staining was set to 5% of the total tissue area. 35 patients were designated as Sox-11 high and this group was compared to the Sox-11 low or negative group. Analysis showed that both overall survival (FIG. 6) and time to relapse (FIG. 7) was significant better (p<0.05) for the Sox-11 high group, as compared to the Sox-11 low or negative group.

In summary, cytoplasmic staining of Sox-11 is positively correlated to overall survival and time to relapse in DLBCL.

The invention claimed is:

1. A method of identifying the presence and type of lymphoma cells in an individual and treating the individual for lymphoma, the method comprising:
   (a) providing a sample of cells from the individual;
   (b) contacting the sample of cells with an antibody or antigen-binding fragment capable of selectively binding to Sox11 protein, or a nucleic acid molecule capable of selectively binding to a nucleic acid molecule encoding Sox11 protein;
   (c) determining the amount of Sox11 protein and/or mRNA in the sample of cells; and
   (d) determining the presence and type of lymphoma cells in the individual based on the amount of Sox11 protein and/or mRNA in the sample of cells, wherein nuclear expression of Sox11 protein and/or mRNA is indicative of the individual having lymphoma cells, wherein the lymphoma is a mantle cell lymphoma (MCL); and
   (e) initiating anti-MCL therapy based on the determination in step (d).

2. A method according to claim 1 wherein the method is performed in vitro.

3. A method according to claim 1 wherein Sox11 is used as a sole biomarker.

4. A method according to claim 1 wherein Sox11 is used in combination with one or more additional biomarkers.

5. A method according to claim 1 wherein the sample of cells to be tested is in the form of a tissue sample.

6. A method according to claim 5 wherein the sample of cells to be tested comprises or consists of lymph node cells.

7. A method according to claim 1 wherein step (b) is performed using a method selected from the group consisting of macroarray screening, microarray screening, nanoarray screening, reverse transcription PCR, real-time PCR or in situ PCR.

8. A method according to claim 1 further comprising determining the levels of CD23 and/or CD10 and/or BCL1 and/or CD5 protein and/or mRNA in the sample of cells to be tested.

9. An ex vivo method of imaging lymphoma cells from the body of a human individual and treating the individual for lymphoma, the method comprising the steps of:
   (a) providing a sample of cells from the individual;
   (b) administering to the sample an effective amount of an antibody or antigen binding fragment which is capable of binding selectively to Sox11 protein, or a nucleic acid molecule which selectively binds a nucleic acid molecule encoding Sox11 protein wherein the lymphoma is a mantle cell lymphoma (MCL) said selectively binding antibody or antigen binding fragment and said selectively binding nucleic acid molecule comprising a detectable moiety; and (c) detecting the location of said antibody or antigen binding fragment, or said nucleic acid molecule; and (d) initiating anti-MCL therapy based on the detection in step (c).

10. The ex vivo method of claim 9, wherein said Sox11 antigen binding fragment is selected from the group consisting of Fab, F(ab')$_2$, and Fv, antigen binding fragment.

* * * * *